United States Patent
Tracy

(10) Patent No.: US 8,060,328 B2
(45) Date of Patent: Nov. 15, 2011

(54) METHOD AND APPARATUS FOR QUANTITATING SURFACE-BINDING OPTICAL RESONANCE PROFILES

(75) Inventor: David H. Tracy, Norwalk, CT (US)

(73) Assignee: GE Healthcare Bio-Sciences AB, Uppsala (SE)

( * ) Notice: Subject to any disclaimer, the term of this patent is extended or adjusted under 35 U.S.C. 154(b) by 0 days.

(21) Appl. No.: 12/881,403

(22) Filed: Sep. 14, 2010

(65) Prior Publication Data

US 2010/0332174 A1    Dec. 30, 2010

Related U.S. Application Data

(63) Continuation of application No. 10/566,306, filed as application No. PCT/US2004/024788 on Aug. 2, 2004, now Pat. No. 7,822,568.

(60) Provisional application No. 60/492,061, filed on Aug. 1, 2003.

(51) Int. Cl.
G01R 9/00      (2006.01)
G01R 9/04      (2006.01)
G01C 7/00      (2006.01)
G01F 25/00     (2006.01)

(52) U.S. Cl. .............. 702/85; 702/91; 702/93; 702/100

(58) Field of Classification Search .................... 702/19, 702/20, 27, 82, 85, 104, 127, 138, 179, 182, 702/183; 250/339.09; 257/680; 356/73, 356/138, 432; 385/12
See application file for complete search history.

(56) References Cited

U.S. PATENT DOCUMENTS

| 5,303,165 | A |   | 4/1994  | Ganz et al. |
|-----------|---|---|---------|-------------|
| 5,308,982 | A |   | 5/1994  | Ivaldi et al. |
| 5,313,264 | A | * | 5/1994  | Ivarsson et al. .................. 356/73 |
| 5,925,878 | A |   | 7/1999  | Challener |
| 5,956,355 | A | * | 9/1999  | Swanson et al. ................. 372/20 |
| 6,029,115 | A | * | 2/2000  | Tracy et al. ..................... 702/22 |
| 6,384,473 | B1| * | 5/2002  | Peterson et al. .............. 257/680 |
| 6,549,687 | B1| * | 4/2003  | Kochergin et al. .............. 385/12 |
| 6,707,043 | B2| * | 3/2004  | Coates et al. ............. 250/339.09 |
| 6,791,691 | B2|   | 9/2004  | Ohtsuka et al. |
| 6,819,812 | B2| * | 11/2004 | Kochergin et al. .............. 385/12 |

(Continued)

FOREIGN PATENT DOCUMENTS

WO     WO 99/30135     6/1999

OTHER PUBLICATIONS

Chandezon et al., *Journal of the Optical Society of America*, 72: 839-846 (1982).

(Continued)

*Primary Examiner* — Michael Nghiem
*Assistant Examiner* — Felix Suarez

(57) ABSTRACT

An apparatus for quantitation of surface-binding optical resonance profiles includes a calibration module including a calibration scan result fetcher, a calibration profile creation module, and a fitting module. The fitting module includes an experimental scan result fetcher, a calibration profile fetcher, and a resonance shift determination module. A method for qualifying a surface plasmon resonance chip is also described herein.

15 Claims, 18 Drawing Sheets

U.S. PATENT DOCUMENTS

| | | | |
|---|---|---|---|
| 6,825,922 B2 * | 11/2004 | Johnston et al. | 356/138 |
| 7,015,471 B2 * | 3/2006 | Franzen et al. | 250/338.1 |
| 7,102,754 B2 | 9/2006 | Ohtsuka et al. | |
| 7,283,242 B2 * | 10/2007 | Thornton | 356/432 |
| 7,417,737 B2 * | 8/2008 | Kuruma et al. | 356/445 |
| 7,822,568 B2 * | 10/2010 | Tracy | 702/85 |
| 2003/0180820 A1 * | 9/2003 | Bar-Or et al. | 435/7.32 |

OTHER PUBLICATIONS

Cush et al., *Biosensors & Bioelectronics*, 8(7/8): 347-353 (1993).
Lawrence et al., *Biosensors & Bioelectronics*, 11: 389-400 (1996).
Salamon et al., *Biophysical Journal*, 73: 2791-2797 (1997).
Tiefenthaler et al., *Biosensors Bioelectron.*, 8: xxxv-xxxvii (1993).
Zizlsperger et al., *Progr. Colloid Polym. Sci.*, 109: 244-253 (1998).

* cited by examiner

| Date/Time | Application | Severity | User | Module | Data | Description |
|---|---|---|---|---|---|---|
| 1/21/2003 4:58:46 PM | SPR | Warning | None | EPF_IF | | Bad Profiles in EPF Calibration |
| 1/21/2003 4:58:31 PM | SPR | Information | None | SPR_APP | | ChipSetupPage::OnFluidicsStateChange(idle) |
| 1/21/2003 4:58:31 PM | SPR | Information | None | SPR_APP | | ChipSetupPage::OnFluidicsStateChange(busy) |
| 1/21/2003 4:13:21 PM | SPR | Information | None | SPR_APP | | ChipSetupPage::OnFluidicsStateChange(idle) |
| 1/21/2003 3:52:52 PM | SPR | Recoverable E... | None | EPF_IF | x | Fit Error ROI:37 Reason: SPRfit Amplitude Tiny Or Negative |
| 1/21/2003 3:52:52 PM | SPR | Recoverable E... | None | EPF_IF | x | Fit Error ROI:32 Reason: SPRfit Amplitude Tiny Or Negative |
| 1/21/2003 3:52:52 PM | SPR | Recoverable E... | None | EPF_IF | x | Fit Error ROI:29 Reason: SPRfit Amplitude Tiny Or Negative |
| 1/21/2003 3:52:52 PM | SPR | Recoverable E... | None | EPF_IF | x | Fit Error ROI:28 Reason: SPRfit Amplitude Tiny Or Negative |
| 1/21/2003 3:52:52 PM | SPR | Recoverable E... | None | EPF_IF | x | Fit Error ROI:27 Reason: SPRfit Amplitude Tiny Or Negative |
| 1/21/2003 3:52:52 PM | SPR | Recoverable E... | None | EPF_IF | x | Fit Error ROI:10 Reason: SPRfit Amplitude Tiny Or Negative |
| 1/21/2003 3:52:52 PM | SPR | Recoverable E... | None | EPF_IF | x | Fit Error ROI:9 Reason: SPRfit Amplitude Tiny Or Negative |
| 1/21/2003 3:52:52 PM | SPR | Recoverable E... | None | EPF_IF | x | Fit Error ROI:8 Reason: SPRfit Amplitude Tiny Or Negative |
| 1/21/2003 3:52:52 PM | SPR | Recoverable E... | None | EPF_IF | x | Fit Error ROI:5 Reason: SPRfit Amplitude Tiny Or Negative |
| 1/21/2003 3:52:47 PM | SPR | Information | None | SPR_APP | | ChipSetupPage::OnFluidicsStateChange(busy) |
| 1/21/2003 3:52:47 PM | SPR | Information | None | SPR_APP | | Calling EndRun |
| 1/21/2003 3:52:45 PM | SPR | Recoverable E... | None | EPF_IF | x | Fit Error ROI:37 Reason: Less Than 3 Points Available For Fit Af... |
| 1/21/2003 3:52:45 PM | SPR | Recoverable E... | None | EPF_IF | x | Fit Error ROI:32 Reason: SPRfit Amplitude Tiny Or Negative |
| 1/21/2003 3:52:45 PM | SPR | Recoverable E... | None | EPF_IF | x | Fit Error ROI:29 Reason: SPRfit Amplitude Tiny Or Negative |
| 1/21/2003 3:52:45 PM | SPR | Recoverable E... | None | EPF_IF | x | Fit Error ROI:28 Reason: SPRfit Amplitude Tiny Or Negative |
| 1/21/2003 3:52:45 PM | SPR | Recoverable E... | None | EPF_IF | x | Fit Error ROI:27 Reason: SPRfit Amplitude Tiny Or Negative |
| 1/21/2003 3:52:45 PM | SPR | Recoverable E... | None | EPF_IF | x | Fit Error ROI:10 Reason: SPRfit Amplitude Tiny Or Negative |
| 1/21/2003 3:52:45 PM | SPR | Recoverable E... | None | EPF_IF | x | Fit Error ROI:9 Reason: SPRfit Amplitude Tiny Or Negative |
| 1/21/2003 3:52:45 PM | SPR | Recoverable E... | None | EPF_IF | x | Fit Error ROI:8 Reason: SPRfit Amplitude Tiny Or Negative |
| 1/21/2003 3:52:45 PM | SPR | Recoverable E... | None | EPF_IF | x | Fit Error ROI:5 Reason: SPRfit Amplitude Tiny Or Negative |
| 1/21/2003 3:52:38 PM | SPR | Recoverable E... | None | EPF_IF | x | Fit Error ROI:37 Reason: Less Than 3 Points Available For Fit Af... |
| 1/21/2003 3:52:38 PM | SPR | Recoverable E... | None | EPF_IF | x | Fit Error ROI:32 Reason: SPRfit Amplitude Tiny Or Negative |
| 1/21/2003 3:52:38 PM | SPR | Recoverable E... | None | EPF_IF | x | Fit Error ROI:29 Reason: SPRfit Amplitude Tiny Or Negative |
| 1/21/2003 3:52:38 PM | SPR | Recoverable E... | None | EPF_IF | x | Fit Error ROI:28 Reason: SPRfit Amplitude Tiny Or Negative |
| 1/21/2003 3:52:38 PM | SPR | Recoverable E... | None | EPF_IF | x | Fit Error ROI:27 Reason: SPRfit Amplitude Tiny Or Negative |
| 1/21/2003 3:52:38 PM | SPR | Recoverable E... | None | EPF_IF | x | Fit Error ROI:10 Reason: SPRfit Amplitude Tiny Or Negative |
| 1/21/2003 3:52:38 PM | SPR | Recoverable E... | None | EPF_IF | x | Fit Error ROI:9 Reason: SPRfit Amplitude Tiny Or Negative |
| 1/21/2003 3:52:38 PM | SPR | Recoverable E... | None | EPF_IF | x | Fit Error ROI:8 Reason: SPRfit Amplitude Tiny Or Negative |
| 1/21/2003 3:52:38 PM | SPR | Recoverable E... | None | EPF_IF | x | Fit Error ROI:5 Reason: SPRfit Amplitude Tiny Or Negative |
| 1/21/2003 3:52:31 PM | SPR | Recoverable E... | None | EPF_IF | x | Fit Error ROI:37 Reason: SPRfit Amplitude Tiny Or Negative |
| 1/21/2003 3:52:31 PM | SPR | Recoverable E... | None | EPF_IF | x | Fit Error ROI:32 Reason: SPRfit Amplitude Tiny Or Negative |
| 1/21/2003 3:52:31 PM | SPR | Recoverable E... | None | EPF_IF | x | Fit Error ROI:29 Reason: SPRfit Amplitude Tiny Or Negative |
| 1/21/2003 3:52:31 PM | SPR | Recoverable E... | None | EPF_IF | x | Fit Error ROI:28 Reason: SPRfit Amplitude Tiny Or Negative |
| 1/21/2003 3:52:31 PM | SPR | Recoverable E... | None | EPF_IF | x | Fit Error ROI:27 Reason: SPRfit Amplitude Tiny Or Negative |
| 1/21/2003 3:52:31 PM | SPR | Recoverable E... | None | EPF_IF | x | Fit Error ROI:10 Reason: SPRfit Amplitude Tiny Or Negative |
| 1/21/2003 3:52:31 PM | SPR | Recoverable E... | None | EPF_IF | x | Fit Error ROI:9 Reason: SPRfit Amplitude Tiny Or Negative |
| 1/21/2003 3:52:31 PM | SPR | Recoverable E... | None | EPF_IF | x | Fit Error ROI:8 Reason: SPRfit Amplitude Tiny Or Negative |
| 1/21/2003 3:52:31 PM | SPR | Recoverable E... | None | EPF_IF | x | Fit Error ROI:5 Reason: SPRfit Amplitude Tiny Or Negative |
| 1/21/2003 3:52:24 PM | SPR | Recoverable E... | None | EPF_IF | x | Fit Error ROI:37 Reason: SPRfit Amplitude Tiny Or Negative |
| 1/21/2003 3:52:24 PM | SPR | Recoverable E... | None | EPF_IF | x | Fit Error ROI:32 Reason: SPRfit Amplitude Tiny Or Negative |
| 1/21/2003 3:52:24 PM | SPR | Recoverable E... | None | EPF_IF | x | Fit Error ROI:29 Reason: SPRfit Amplitude Tiny Or Negative |

FIG. 17

METHOD AND APPARATUS FOR QUANTITATING SURFACE-BINDING OPTICAL RESONANCE PROFILES

CROSS-REFERENCE TO RELATED APPLICATION

This application is a continuation of U.S. patent application Ser. No. 10/566,306 filed Jan. 27, 2006, now U.S. Pat. No. 7,822,568, issued Oct. 26, 2010, which is a filing under 35 U.S.C. §371 and claims priority to international patent application number PCT/US2004/024788 filed Aug. 2, 2004, published on Mar. 31, 2005, as WO 2005/029031, which claims priority to U.S. Provisional Application Ser. No. 60/492,061, filed Aug. 1, 2003.

FIELD OF THE INVENTION

This invention relates to data quantitation methods and, in particular, to quantitation of data profiles obtained using optical resonance surface sensors.

BACKGROUND OF THE INVENTION

Optical resonance surface sensors are utilized in a number of chemical, pharmacological, and biotechnology research fields, including proteomics and drug discovery. Quantitation of surface-binding optical resonance profiles, such as Surface Plasmon Resonance (SPR) profiles, allows real-time observation and analysis of molecular interactions, providing data uninfluenced by biochemical labeling. As a consequence, optical resonance surface sensors have become widely used for the characterization of biological surfaces and the real-time monitoring of binding events.

At the present time, the most commonly used optical resonance surface sensors detect SPR. Surface plasmons are transverse electromagnetic charge-density waves that propagate parallel to the interface between a dielectric medium and a metallic film. Surface plasmons are generated by the interaction between the electron-rich surface of the metal and a charged particle or photon. Under appropriate conditions, the plasmons will resonate with light, resulting in the absorption of light.

More specifically, at an interface between two transparent media of different refractive index, light coming from the side having higher refractive index is partly reflected and partly refracted. Above a certain angle of incidence, no light is refracted across the interface and total internal reflection (TIR) is observed. While incident light is totally reflected, the electromagnetic field component does penetrate a short distance, on the order of tens or hundreds of nanometers, into a medium of lower refractive index, thus creating an exponentially detenuating evanescent wave. If the interface between the media is coated with a thin layer of metal, and the incident light is monochromatic and p-polarized, the intensity of the reflected light is reduced at a specific incident angle. This produces surface plasmon resonance due to the resonance energy transfer between the evanescent wave and the surface plasmons.

Many SPR sensors utilize the Kretschmann or Otto configurations, wherein the evanescent wave from totally internally reflected monochromatic light traveling through a prism creates a surface plasmon in a metal film that is in contact with the material to be detected. In these configurations, the light is incident on the metal film through the prism at an angle greater than a critical angle, known as the resonant angle $\theta_{SPR}$. The surface plasmon is then detected by adjusting the angle of incidence until a sharp decrease in the reflected intensity is detected. If the permittivity or thickness of the dielectric layer changes, the resonant angle also changes.

In another common SPR configuration, the light is incident from the sample side of the metal film and is coupled to the surface to create the plasmon resonance by means of a diffraction grating in the metal surface. In still another SPR configuration, the metal film is deposited on the outside of an optical fiber or other waveguide and light is coupled into and out of the surface through the waveguide.

The existence of the SPR is detected by measurement of the intensity of the reflected light from the dielectric/metal interface, either from the back side (Kretschmann case) or the sample side (Otto and grating coupled cases). The resonance condition is sensitive to the effective refractive index of the medium adjacent to the metal film, and hence to the configuration of its surface. The term effective refractive index is used here because, if there is also a very thin (<<1 μm) solid biolayer in addition to the bulk fluid layer, then the biolayer will change the SPR angle and therefore cause the appearance of a change in the fluid refractive index. This is the common case, where both the biofilm and the bulk fluid refractive index affect the signal. Essentially, everything in the evanescent layer a few hundred nanometers thick has an influence. The surface configuration is therefore also changed by any material adsorbed onto the metal film, so that the binding of biomolecules to the film results in a change of the effective refractive index of the dielectric. Because of this, adsorption of molecules on the metallic film or conformational changes in the adsorbed molecules can be accurately detected. SPR imaging can therefore be used to detect the presence and/or amount of a biopolymer on a chemically modified metal surface by quantitation of the change in the local index of refraction that occurs upon adsorption.

For monochromatic or quasi-monochromatic illumination, the SPR angle will change directly according to the amount of bound materials; there is a linear relationship between the amount and the observed shift of the resonant angle. In particular, a linear relationship has been established between resonance angle and the mass concentration of biochemically relevant molecules such as proteins, sugars, and DNA. An SPR signal expressed in terms of angle shifts, or other units proportional to such shifts, is therefore a measure of mass concentration at the sensor chip surface. This means that analyte and ligand association and disassociation can be observed and rate and equilibrium constants may be calculated.

In an alternative SPR configuration, a fixed angle of incidence is employed and the wavelength of the exciting light is varied, or a broadband optical source is employed together with an array spectrometer. With this approach, the SPR appears as a dip in the reflected intensity as a function of wavelength, with the wavelength of the SPR minimum varying linearly as a function of mass concentration at the chip surface. This configuration can be employed with any of the coupling mechanisms previously described (prism, grating, or waveguide).

Surface plasmon resonance instruments may measure mass loading at a single spot, at several spots, or simultaneously at a large array of spots on an experimental surface (chip). In the case of an array instrument, the individual zones within which SPR shifts are measured are called Regions of Interest (ROIs).

The output of an SPR apparatus, whether the independent variable is angle or wavelength, is typically a graphed resonance curve. The location of the SPR resonance indicates the effective refractive index of the material on the sensor. Several approaches to SPR resonance curve shift quantitation have previously been utilized including, but not limited to:

(1) 1st moment below a baseline
(2) point of specific reflectance/signal
(3) polynomial fit about the minimum
(4) zero-crossing of the first derivative
(5) reflectance/signal at a specific point
(6) nonlinear fits of analytic functions Some literature distinguishes between Absolute Refractive Index (RI) measurements and Relative RI measurements. The basis of this distinction is not entirely clear, since any precise absolute measurements must involve comparison with an RI standard. It is true, however, that, if a system is to be calibrated once and then used over time for absolute RI measurements, some algorithms are more suitable than others. This is due, for example, to such things as reduced sensitivity to sensor fouling or to baseline shifts. There also may be occasions where only changes in the refractive index are of interest. The same considerations apply, albeit to a reduced degree, to relative RI measurements of the sort required for measuring binding curves.

The position of the SPR curve minimum is the most common indicator of the absolute refractive index. The polynomial fit about the minimum (method (3)) and zero-crossing of the first derivative (method (4)) methods specifically determine this position. The other methods look at other aspects of the SPR curve in order to determine the minimum. Advantages of measuring absolute RI are that it looks at the SPR curve minimum, the measurement is insensitive to vertical shifts of the SPR curve (along the SPR signal axis), and the measurement is insensitive to fouling of the SPR sensor surface (which degrades the smoothness of the SPR curve). Disadvantages include that the measurement can be sensitive to the choice of points included in the analysis, potentially leading to distortion of the readings due to noise.

Prior to performing any of the analysis methods, it is possible to smooth the SPR curve. This can lead to reduced noise when tracking refractive index versus time. One common smoothing algorithm is a least-squares smooth, which typically incorporates from 1 to 12 points on either side of a point when determining the smoothed value of that point. Since smoothing does effectively bring multiple data points to bear on each smoothed point, algorithms which nominally depend on only one or a small number of data points may possibly be helped by smoothing procedures. In most cases, however, smoothing offers little or no benefit in well-designed fitting procedures, and can even hurt.

(1) 1st Moment Below a Baseline Method

The first moment method calculates the first moment of the SPR curve below a baseline. That is, only those parts of the SPR curve that are below the baseline are included in the calculation. For the simple case of n equally spaced data points, the algorithm may be expressed as:

$$1st \text{ moment} = \frac{\sum_{i=1}^{n} |SPRsignal_i - Baseline| * i}{\sum_{i=1}^{n} |SPRsignal_i - Baseline|}$$

where the summations exclude all data points where the SPR signal is greater than the baseline.

As long as the curve doesn't vertically shift, the algorithm will accurately track changes in the refractive index. Choosing where to set the baseline is not obvious. Frequently, the baseline is set at the midpoint of the SPR dip. Lowering the baseline will include fewer points in the analysis and may lead to increased noise. Raising the baseline includes more points, but the resulting calculation will deviate even more from the curve minimum. If the points selected for the analysis begin to shift out of the sensor range, the analysis will be degraded. There also may be times when an anomaly appears in the SPR curve, perhaps due to sensor surface fouling. It is still possible to use the sensor, so long as the anomaly is not near the SPR dip. To deal with this situation, various regions may be selectively excluded from the analysis. Thus, even if the anomaly is below the baseline, an accurate measurement results because the anomaly is excluded from the calculation.

This technique can exhibit good performance with respect to shot noise or other similar random additive noises, in part because it involves a large number of points and a very simple algorithm. A helpful addition is the provision of interpolation calculations at the baseline cutoff levels on either wing to handle the fact that baselines will rarely pass directly through data points. Smoothing of these cutoff zones can also be helpful. However, the fundamental disadvantage of the $1^{st}$ moment technique for SPR is its high sensitivity to intensity or signal baseline shifts (vertical shifts of the SPR curve) due to the inherent asymmetry of SPR resonances. High data point density is therefore required. This method also tends to be sensitive to sensor surface fouling.

(2) Point of Specific Reflectance/Signal

The point of specific reflectance/signal method utilizes the pixel position at which the SPR curve is a pre-specified value. The curve is initially examined in order to approximately locate the data point where the curve is closest to the specified value. An nth order polynomial least squares fit is then performed in order to interpolate and identify exactly where on the curve the value occurs. The search may be done from either the left or the right side of the curve. As the SPR curve shifts along the x-axis, the identified point will follow this shift.

This method is susceptible to alterations in the overall shape of the SPR curve and it does not directly determine the minimum point. Still, it is useful for quantitating small shifts. In addition, it can be utilized to expand the dynamic range of the sensor. For example, if the minimum of the SPR curve is below pixel #1 (off the left side of the sensor range) the sensor may still be employed to track some other point on the SPR curve.

This technique has little to recommend it except simplicity. It suffers from much greater sensitivity to intensity or baseline changes than method (1), as well as being very sensitive to small changes in resonance shape. It uses very little of the resonance curve data for each determination, and thus has poor noise transfer performance. For decent performance, data point spacing must be tight.

Another version of this technique is to perform the calculation on both sides of the resonance and use the mean of the two to track the resonance. This is then similar to method (1), but with poorer noise performance since, again, only a relatively small subset of the data is used. It also has greater sensitivity than method (1) to intensity shifts.

(3) Polynomial Fit About the Minimum

In the polynomial fit about the minimum method, a first pass of the SPR curve is made in order to find the approximate location of the minimum of the resonance. An nth order polynomial least squares fit (using some number of points about the minimum) is then performed in order to interpolate the position of the minimum. This method is suitable for absolute refractive index measurements. This method is not susceptible to y-axis shifting of the SPR curve. However, since it only uses a relatively small number of points on the curve, it can be susceptible to the selection of points to be included in the calculation. This can sometimes lead to occasional anomalies in the analysis results (noise).

This method works fairly well, especially with respect to intensity and baseline shifts, but depends on relatively little data and so exhibits sub-optimal noise transfer performance. As with any method that actually attempts to locate the minimum of the resonance (as opposed to its overall position), it can be sensitive to noise near the bottom. Higher order polynomials, which can better fit the shape of the resonance, allow a wider range of data points to be included, but also offer more opportunity to move the minimum around to accommodate noise on individual data points. In other words, higher order polynomials have excess degrees of freedom that translate into increased noise injection into the shift determination. In practice, tight data point spacing is required, but the needed angle scan range can be fairly limited.

(4) Zero-Crossing of the First Derivative

The zero-crossing of the first derivative method is derived from the fact that the first derivative changes sign about the minimum of the SPR curve. In the zero-crossing algorithm, the approximate minimum point of the SPR curve is initially determined, a linear least-squares fit of the first derivative is performed using a few points about the approximate minimum, and the zero-crossing point is interpolated.

This amounts to a more or less direct determination of the actual minimum of the resonance curve, which is perhaps the least well-defined point on the curve. Many algorithms can be used to estimate the derivative and to find its zero crossing, and most of these do include some inherent smoothing or multi-point fitting, so that mathematically this process can be equivalent, for example, to method (3) (polynomial fit about the minimum). Using Savitsky-Golay derivatives, for example, the process is fully equivalent to method (3). Depending on the detailed implementation, this method can perform as well as method (3), and has much the same advantages and disadvantages. Poorly implemented, it can exhibit very poor noise performance. Again, tight data point spacing is needed. This method is suitable for making absolute refractive index measurements.

(5) Reflectance at a Specific Point

The reflectance/signal at a specific point method does not follow shifts of the SPR curve. It merely looks at the value of the SPR curve at a particular angle (or wavelength) position. If necessary, an nth order polynomial least squares fit is performed in order to interpolate the signal value at the desired Specific Point. This technique has often been used in the academic literature, since it can be utilized in a system without either moving parts or an array detector. It depends on the linearity of the side-wall of a resonance over a modest range of SPR shifts. It is essentially equivalent to method (2) (point of specific reflectance/signal) for small shifts, but, unlike method (2), it cannot accommodate larger shifts. One described implementation uses array detector information in which several data points surrounding the Specific Point are fitted, thereby somewhat improving the noise performance.

(6) Nonlinear Fits of Analytic Functions

Theoretical Responses. It has been common in the academic literature of SPR sensors to compare measured angular response curves with theoretical responses, and in some cases fits to these theoretical curves have been performed as a means of measuring film thicknesses, which amounts to measuring resonance shifts.

A paper from Wolfgang Knoll's laboratory in Mainz [M. Zizlsperger and Wolfgang Knoll, "Multispot parallel on-line monitoring of interfacial binding reactions by surface plasmon microscopy", *Progr. Colloid Polym. Sci.*, 109: 244-253 (1998)] shows diagrams (FIGS. 2 and 5) which appear to represent fits of experimental SPR angle response curves to simple Fresnel multilayer theory. The fits are fairly poor, but would suffice to measure resonance shifts. There is no discussion of the fitting method. Possible methods include manual trial and error parameter adjustment, or non-linear methods such as Levenberg-Marquardt.

A paper on Grating SPR sensors [C. R. Lawrence, N. J. Geddes, D. N. Furlong, J. R. Sambles, "Surface Plasmon resonance studies of immunoreactions utilizing disposable diffraction gratings", *Biosensors & Bioelectronics*, 11: 389-400 (1998)] shows fits of experimental data to GSPR theory using a coupled wave method [J. Chandezon, M. T. Dupuis, G. Cornet, and D. Maystre, "Multicoated gratings: a differential formalism applicable in the entire optical region", *JOSA*, 72: 839-846 (1982)]. The fitting procedure is not described, but could be a conventional non-linear least squares fit. It is stated that the fit involves a large number of parameters, including the optical constants of gold, the pitch and groove depth of the grating, and a groove distortion factor, as well as the thickness and (sometimes) the optical properties of an adsorbed protein layer. In some cases, certain of these parameters may be fixed. The fits are very good, indicating that great care was taken experimentally to avoid distortions and artifacts.

These techniques are in principle capable of very good results for SPR shift quantitation, provided that the number of free parameters is kept small. In other words, if a preliminary fit were used to establish all of the parameters except for the adlayer thickness, and subsequent run-time fits left only the thickness and a couple of amplitude scaling parameters free, then performance should be reasonably good.

Some downsides to this approach are:

a) The model calculations are very complex and intensive, particularly for the GSPR case.

b) Nonlinear fits themselves are very compute intensive (beyond the necessary theoretical model evaluations embedded therein), and exhibit instabilities that complicate automated operation.

c) In practice, frequent deviations of resonance shapes from the theoretical ideal are observed. Indeed, the data of Zizlsperger et al. show rather poor fits.

Explicit Functions. Yet another approach that has been suggested is non-linear fitting of relatively tractable explicitly defined mathematical functions to the run-time data. Unlike the Theoretical Responses, which are numerical profiles resulting from a complex computational process for a given set of input parameters, such explicit functions could be computed cheaply and are therefore much more attractive. In a way, this is an extension of the polynomial fitting approach, although polynomials have the property of allowing fast linear least squares fits.

If functional forms could be identified that have the flexibility to fit well to the range of observed profile shapes, this approach can work well. The downsides are:

a) The difficulty of identifying such functional forms, unless we restrict the fits to a small region around the minimum, in which case see Polynomial Fits, above. As a corollary, the difficulties of ensuring that future oddities in profile shapes that are not modelable by the chosen functional form do not occur.

b) The need, in general, for non-linear least squares or other non-linear fitting procedures.

c) Degraded noise performance due to the extra shape parameters likely needed to represent the full range of observed profiles. This problem can be sidestepped by the approach suggested above, in which a preliminary fit is used to fix most of the free parameters, leaving only resonance shift and amplitude(s) as fitting parameters.

Although most of the foregoing discussion has been about the most commonly utilized form of surface-binding optical resonance, SPR, optical resonance curves obtained from other types of surface-binding optical resonances are quantitated in a similar fashion. Examples of devices and techniques for measuring such resonances include optical waveguide sensors (such as the BIOS-1 angle scanned grating coupled optical waveguide instrument currently made by Artificial Sensing Instruments AG), grating couplers (K. Tiefenthaler (1993) "Grating couplers as label-free biochemical waveguide sensors", *Biosensors Bioelectron.*, 8:xxxv-xxxvii), plasmon waveguide resonance devices (Z. Salamon, H. A. Macleod and G. Tollin (1997) "Coupled Plasmon-Waveguide Resonators: A New Spectroscopic Tool of Probing Film Structure and Properties", *Biophysical Journal*, 73:2791-2797), diffraction anomaly sensors (U.S. Pat. No. 5,925,878, Challener, 2000, "Diffraction anomaly sensor having grating coated with protective dielectric layer"), resonant mirror devices (R. Cush et al. (1993) "The Resonant Mirror: a Novel Optical Biosensor for Direct Sensing of Biomolecular Interactions", *Biosensors & Bioelectronics* 8(7/8): 347-353), long range SPR (http://plazmon.ure.cas.cz/tobiska/optsen01.pdf), and the Perkin Elmer optical resonance analysis system described in WO 99/30135 (Tracy et al., published Jun. 17, 1999). To some extent, these devices and techniques are variations on two themes—dielectric planar waveguides and metal film SPR, or combinations thereof. All require no fluorescent label and are often called biosensors, but they are not restricted in their application to characterization of biofilms.

What has been needed, therefore, is a way to quantitate surface-binding optical resonance curves that requires low computational complexity and a minimal number of scan data points while still providing accurate determination of the resonance angle and good noise performance. This ability will in turn allow for longer scan times and/or scans over a greater number of ROIs, enhancing the utility of optical resonance surface sensor techniques for the observation of, for example, such phenomena as adsorption onto chemically modified metal surfaces, binding events involving biological molecules such as DNA, proteins, enzymes, and antibodies, and immunologic phenomena such as antigen-antibody reactions and antigen stimulation of tissue.

OBJECTS OF THE INVENTION

Accordingly, an object of the present invention is to provide a new mechanism for accurate quantitation of surface-binding optical resonance curves.

A particular object of the invention is to provide a method for quantitation of surface-binding optical resonance curves that has relatively low computational complexity.

A further particular object of the present invention is to provide a method for quantitation of surface-binding optical resonance curves that requires a minimal number of scan data points.

Another particular object of the invention is to provide a mechanism for quantitation of surface-binding optical resonance curves that is less sensitive to shot noise.

Yet another particular object of the invention is to accommodate the use of long surface-binding optical resonance scan times.

Still another particular object of the invention is to provide a mechanism for quantitation of surface-binding optical resonance curves that provides increased scan speeds.

Another particular object of the invention is to provide the ability to obtain surface-binding optical resonance results for a sample more quickly than is presently possible.

Still a further particular object of the invention is to accommodate surface-binding optical resonance scans over a greater number of ROIs.

A further particular object of the invention is to provide valid extension of the dynamic range of surface-binding optical resonance scans, so that useful results may be obtained even when only partial resonance curves are available due to limitations on the angular scanning range employed.

SUMMARY OF THE INVENTION

These and other objectives are met by the present invention in which Empirical Profile Fits (EPF) are used to quantitate surface-binding optical resonance profiles. The EPF method and apparatus use observed surface-binding optical resonance profiles at a relatively fine angle or wavelength spacing to create an empirical functional form. In the preferred embodiment, surface-binding optical resonances to be quantitated are then fit by a three parameter model consisting of (a) the empirical profile itself, (b) a numerical derivative of the profile generated using Savitsky-Golay filters, and (c) a constant additive offset to model any baseline shifts or continuum illumination. The shift of the fitted resonance is determined as the ratio of the derivative fit coefficient to the profile fit coefficient. When the shift so determined exceeds a predetermined threshold, the original EPF profile is shifted by Lagrange Interpolation to the approximate location of the resonance, and the fit is re-done.

The EPF peak finding process has two stages, the Calibration stage and the Fit stage. In the Calibration stage, a calibration scan is obtained with relatively fine angle or wavelength spacing over a range sufficient to include full resonance profiles for all regions. Smoothed, subsampled model profiles for each Region of Interest (ROI) are generated, together with first derivative curves and diagnostic information. In the Fit stage, individual ROI scans are used for measurement of resonance shifts relative to the calibration model. The run-time scans may be at much coarser angle or wavelength spacing, may cover entirely different angle or wavelength ranges than the calibration data, may have either scan polarity and need not encompass the entire surface-binding optical resonance profile. Estimates of peak position can be made even from fragmentary data on one side of the resonance, so that useful results may be obtained even when only partial curves are available. A minimum of three data points is needed for each determination, although normally more points are used. Resonance shifts, estimated absolute angles or wavelengths, time of resonance minimum, and additional diagnostic and quality information are returned. Data obtained from either calibration or fit runs may optionally be exported for analysis using other systems.

In the preferred embodiment, the two stages of the process involved in EPF peak finding are implemented via two separate modules in software, the Calibration module and the Fit module. When a new chip is put into service, or a new calibration is desired on an old chip, a calibration scan is performed. During the calibration scan, surface-binding optical resonance data are obtained under static conditions over a relatively long angle or wavelength range, with relatively small angle or wavelength steps. The raw scans obtained during the calibration scan, one for each ROI being calibrated, are then optionally smoothed and subsampled to increase the point density. In the preferred embodiment, Lagrange or spline interpolation is used to implement the subsampling. Derivatives of the subsampled profiles are computed, using a Savitsky-Golay filter or any other suitable method known in the art. Properties of the profiles are then calculated, including, but not limited to, approximate resonance position, depth, and width. These results are then stored in preparation for later fitting procedures.

In the Fit stage, angle or wavelength scans are measured for particular ROIs during an experiment. These scans may be obtained at much lower point density than the calibration scans, possibly over shorter angle or wavelength ranges. The role of the fitting module is to look at these experimental scans, identify the region encompassing the resonance, and fit that region using the previously stored empirical profiles in order to quantify and return the desired values, including the shift in the resonance as compared to its angular location at calibration time. While absolute angular positions or wavelengths generally cannot be measured accurately, since the resonance position is itself not well defined, rough values can be obtained by adding the shifts to the nominal peak location determined during calibration, and these are also returned.

In a preferred embodiment of the EPF calibration and fitting system, the Instrument Control and Data Acquisition Software gets and sets internal parameters in the EPF Calibration module and then sends raw data from a calibration scan to the EPF Calibration module, which funnels the data through a Subsampler and a Savitsky-Golay smoothing routine before taking derivatives and characterizing the data to create a model calibration profile for the chip being scanned. The model calibration profiles are then optionally stored. Next, the Instrument Control and Data Acquisition Software gets and sets internal parameters in the EPF Fitting module and then sends raw data from a run-time scan performed utilizing the chip to the EPF Fitting module, which qualifies it, queries the EPF Calibration module for the model profile for the chip, and then fits the curve utilizing various matrix routines, iterating the process when necessary. Results from the fitting process are then returned to the Instrument Control and Data Acquisition Software, which provides them to the user.

BRIEF DESCRIPTION OF THE DRAWINGS

FIG. 17 is a screenshot depicting an example embodiment of a local error log, showing reports of bad fits to particular ROIs.

DETAILED DESCRIPTION

Figure 1:
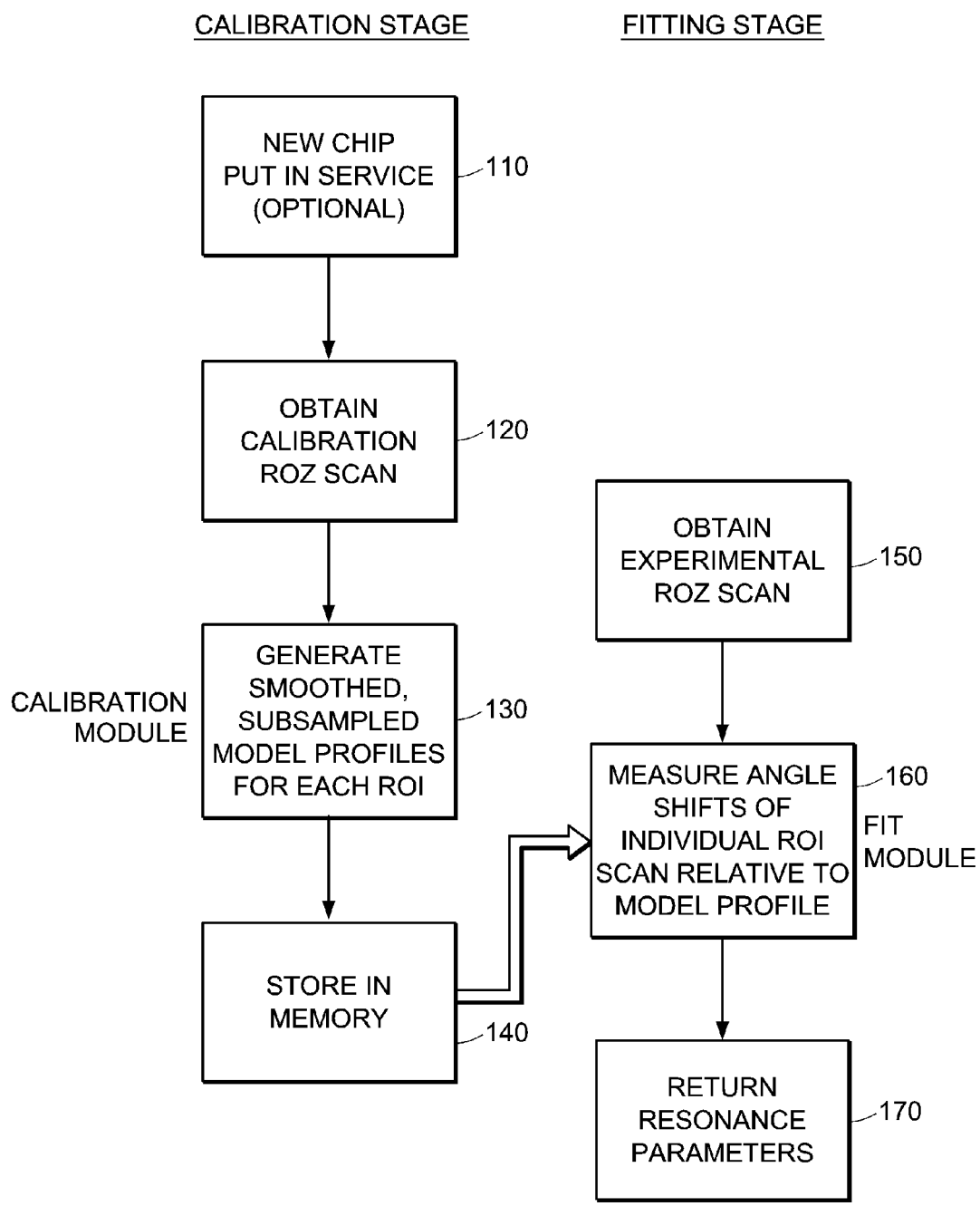
FIG. 1 illustrates the steps of an embodiment of the method for quantitating surface-binding optical resonance profiles according to the present invention.

The current invention utilizes Empirical Profile Fits (EPF) to quantitate surface-binding optical resonance profiles. The EPF peak finding process has two stages, the Calibration stage and the Fit stage. In the Calibration stage, a calibration scan is obtained with relatively fine angle or wavelength spacing over a range sufficient to include full resonance profiles for all regions. Smoothed, subsampled model profiles for each Region of Interest (ROI) are generated, together with first derivative curves and certain diagnostic information. In the Fit stage, individual ROI scans are used for measurement of angle or wavelength shifts relative to the calibration model. The run time scans may be at much coarser angle spacing, may cover entirely different angle ranges than the calibration data, and may have either scan polarity. Resonance shifts, estimated absolute angles or wavelengths, time of resonance minimum, and additional diagnostic and quality information are returned.

Some precursors of certain components of the empirical profile fit of the present invention are disclosed in two prior patents. The use of derivatives in a fit to more accurately calculate and correct for wavelength shifts is disclosed in U.S. Pat. No. 5,303,165 (Ganz et al., 1994) at column 11, line 1, to column 16, line 40; and U.S. Pat. No. 5,308,982 (Ivaldi et al., 1994) at column 3, line 27, to column 5, line 43. In addition, the general idea of using empirical profiles for fitting has been disclosed for use in other contexts. For example, while the words "empirical profile" are not used, a somewhat similar idea is described in U.S. Pat. No. 5,308,982 at column 3, line 46, as a model matrix of known form.

Empirical Profile Fits have been experimentally shown to work at least as well as, or better than, polynomial fits in quantitating Surface Plasmon Resonance profiles. Shot noise limited performance is typically a few tens of microdegrees. EPFs have the further advantage of allowing much sparser angular point spacing, which can increase scan speed severalfold. This is especially true when long scans are needed to accommodate a wide range of resonance shifts in certain experiments. EPF SPR quantitation can be used with any implementation of a mechanism for creating and measuring Surface Plasmon Resonances, including, but not limited to, diffraction grating, prism, and waveguide implementations, with either angle or wavelength as the scanning variable. It may also advantageously be used to quantitate shifts of other resonances used for chemical or biochemical surface sensors, such as waveguide sensors and resonant cavity sensors.

For simplicity, the description of the preferred embodiment that follows specifically discusses the parameters used when quantitating results obtained utilizing a grating-coupled angle scan SPR device. However, the EPF quantitation technique of the present invention is not limited to quantitation of data obtained utilizing SPR devices, nor is it limited to quantitation of data obtained utilizing angle scan techniques. The EPF quantitation technique of the present invention may be advantageously employed to quantitate data produced using any of the many varieties of surface-binding optical evanescent wave sensor technologies which employ angle scanning, wavelength scanning, or a combination thereof (such as pre-dispersion or correlated scanning) and which produce resonances similar to SPR resonances that shift in angle or wavelength more or less linearly with surface adlayer mass or binding. Examples of techniques producing resonances suitable for quantitating using EPF include, but are not limited to, the various techniques previously discussed in the Background section.

Some of these techniques may produce sharper or broader resonances than SPR, the resonance position may be more or less sensitive to biolayer mass density, and/or they may exhibit different resonance propagation lengths, allowing for higher or lower ROI densities in array configurations. The EPF procedure still may be applied directly to quantitate resonances produced using any of these techniques. The main difference in application from the preferred embodiment described herein is that the size of angle steps is scaled to the width of the resonances (or, in the less frequently used wavelength mode, the FWHM of the resonances in wavelength units). In addition, while the curves obtained using some of these techniques exhibit positive peaks rather than negative-going dips as resonances, this has no effect on EPF except with respect to the profile acceptance criteria. Further, while various of these sometimes use a label and use the evanescent wave to excite fluorescence, so long as the exciting beam is angle scanned, EPF can still be used, even though diffuse fluorescence is being measured rather than reflected intensity.

In general, the window over which the fit is performed can be adjusted at will, but is usually chosen to cover the main part of the resonance dip, leaving out the far wings. For best results, resonances at each ROI are fitted using Empirical Profiles measured for that ROI. However, good results are also obtained using Empirical Profiles from other ROIs exhibiting similar resonance shapes. The noise performance of EPF is generally very similar to that for analytical profile fits employing the same more or less orthogonal parameters: intensity, resonance shift, and baseline offset.

The EPF procedure does not attempt to measure the absolute location of a resonance, nor does it even include any definition of "resonance center". Rather, it enables precise measurement of shifts or changes of resonance position from the position of the original model resonance. However, in order to simplify interpretation, an "absolute angle" is arbitrarily assigned to the initial model profile, simply by finding a measure of its minimum as the minimum of a parabolic fit to the bottom n points. Typically, n=5. This semi-arbitrary assignment allows reporting of "absolute angles" which are in the ballpark of other measures. The data points used in the EPF fit need not be at the relatively fine angular spacing used during the original calibration scan. In general, any data point spacing may be used which allows at least three points to be found somewhere within the resonance. Using coarser spacing may, however, have an impact on the precision of determination of the resonance angle.

Overview. The currently preferred embodiment of a system for implementation of the present invention is an array system in which a 2-Dimensional Charge Coupled Device (2-D CCD) detector is used to image a sample chip containing 100-400 or more ROIs. Quasi-monochromatic light from a filtered, p-polarized LED (light-emitting diode) is used for illumination. The angle of incidence of the light beam on the chip is varied by mechanically scanning the light source. For each angle of incidence, one or more CCD frame exposures are used to perform a simultaneous measurement of the reflected light intensities for all the members of the ROI array. While the preferred embodiment of the EPF system of the present invention is specifically targeted toward such array systems, it works equally well on single or few channel instruments.

In this embodiment, when a new chip is put into service, or at any other time desired, a calibration scan is obtained with relatively fine angle spacing over an angle range sufficient to include full resonance profiles for all regions. The preferred angle range will depend on the refractive index (RI) of the buffer, any solid films or adlayers present at the sensor surface, the sensor material, and (if applicable) the grating period. For example, when using grating coupling, a gold metal film, aqueous samples, a center wavelength of 875 nm filtered by an Interference Filter to ~4 nm FWHM, and an 840 nm grating groove spacing, the preferred angle range is typically 20°±2°. In a preferred embodiment of the invention, the angle is controllable to millidegrees and can be measured to microdegrees. All these parameters can be adjusted, resulting in different nominal angles and possibly different FWHM of resonances, creating a need for different step sizes. In addition, if Wavelength scan mode is used, step sizes are in wavelength. To convert the example above to Wavelength scan mode directly, the angle is fixed at ~20 degrees and wavelength is scanned roughly from 860 to 890 nm. The resonances would be ~10 nm wide. Similarly, for other Optical Resonance systems, the nominal wavelength, angle, and FWHM might be very different, requiring scaling of the various EPF parameters, but the process remains identical.

In the preferred embodiment, the calibration data set is submitted to the main calibration procedure, epfCal, which generates smoothed, subsampled model profiles for each ROI, together with first derivative curves and certain diagnostic information. This calibration set is kept in memory, and may optionally be archived for future use. Angle step sizes need not be uniform, as actual measured angles are supplied to the main calibration procedure for each data point.

At run time, as experimental kinetic or other data are being obtained, individual ROI scans are submitted to the main run time fit procedure, epfFit, for measurement of angle shifts relative to the calibration model. The run time scans may be at much coarser angle spacing, and may cover entirely different angle ranges than the calibration data. They may also have either scan polarity (i.e., either up or down angle). Actual measured encoder angles must be supplied for each data point, and times of measurement of each data point must also be provided. Angle shifts, estimated absolute angles, time of resonance minimum, and additional diagnostic and quality information are returned.

The run time scans need not encompass the entire SPR profile. Estimates of peak position can be made even from fragmentary data on one side of the resonance. A minimum of three data points is needed for each determination, although normally more points are used. This ability to provide valid "edge info" for SPR scans, so that useful SPR results may be obtained even when only partial curves are available, is one of the many advantages of the present invention. A further advantage may be had by the optional ability to export data obtained from either calibration or fit runs for re-analysis, or additional analysis, using one or more other analysis systems.

The process involved in EPF peak finding naturally divides into two parts, which, in the preferred embodiment, are implemented via two separate modules in software. These are the Calibration stage and the Fit stage. As seen in FIG. 1, when a new chip is put into service 110, or a new calibration is desired on an old chip, a calibration scan 120 is performed. During the calibration scan 120, SPR data are obtained under static conditions over a relatively long angle range, with relatively small angle steps. The choice of what fluid is present on the sample side of the sensor surface depends on what measurements are being performed. The angle range is then chosen to accommodate the refractive index of the fluid. The precise values of these parameters need not be fixed, and can be varied as experience demands, but nominal 0.05 degree steps, as employed in the preferred embodiment, are highly suitable. These steps are referred to as Base Steps and are indexed by Base Index values. Actual angle values obtained from the angular encoder accompany each intensity value. Units for system angles may be degrees or other units. Any linear units are suitable, so long as they are used consistently.

The raw scans obtained during the calibration scan 120, one for each ROI being calibrated, are then optionally smoothed and subsampled 130 to increase the point density by N, where N typically equals 1 to 10. In the preferred embodiment, Lagrange or spline interpolation is used to implement the subsampling, although any other method known in the art would be suitable. Derivatives of the subsampled profiles are computed, using a Savitsky-Golay filter or any other suitable method known in the art. In the preferred embodiment, certain properties of the profiles are then optionally calculated, including, but not limited to, approximate resonance position, depth, and width, in order to qualify the resonances as adequate and correct. These results are then stored 140 in preparation for later fitting procedures.

In the Fit stage, angle scans are measured for particular ROIs during an experiment 150. These scans may be obtained at much lower point density than that of the calibration scans, and possibly over shorter angle ranges. In the preferred embodiment, the actual encoder angle and actual midpoint-of-integration time for each point are provided to the fitting module 160. The role of the fitting module 160 is to look at the experimental scans obtained during the experiment 150, identify the region encompassing the resonance, and fit that region using the previously stored empirical profiles 140 in order to quantify and return 170 the desired values, including the shift in the resonance as compared to its angular location at calibration time. While absolute angular positions generally cannot be measured accurately, since the resonance position is itself not well defined, rough values can be obtained by adding the shifts to the nominal peak location determined during calibration, and these are also returned 170.

Figure 2:
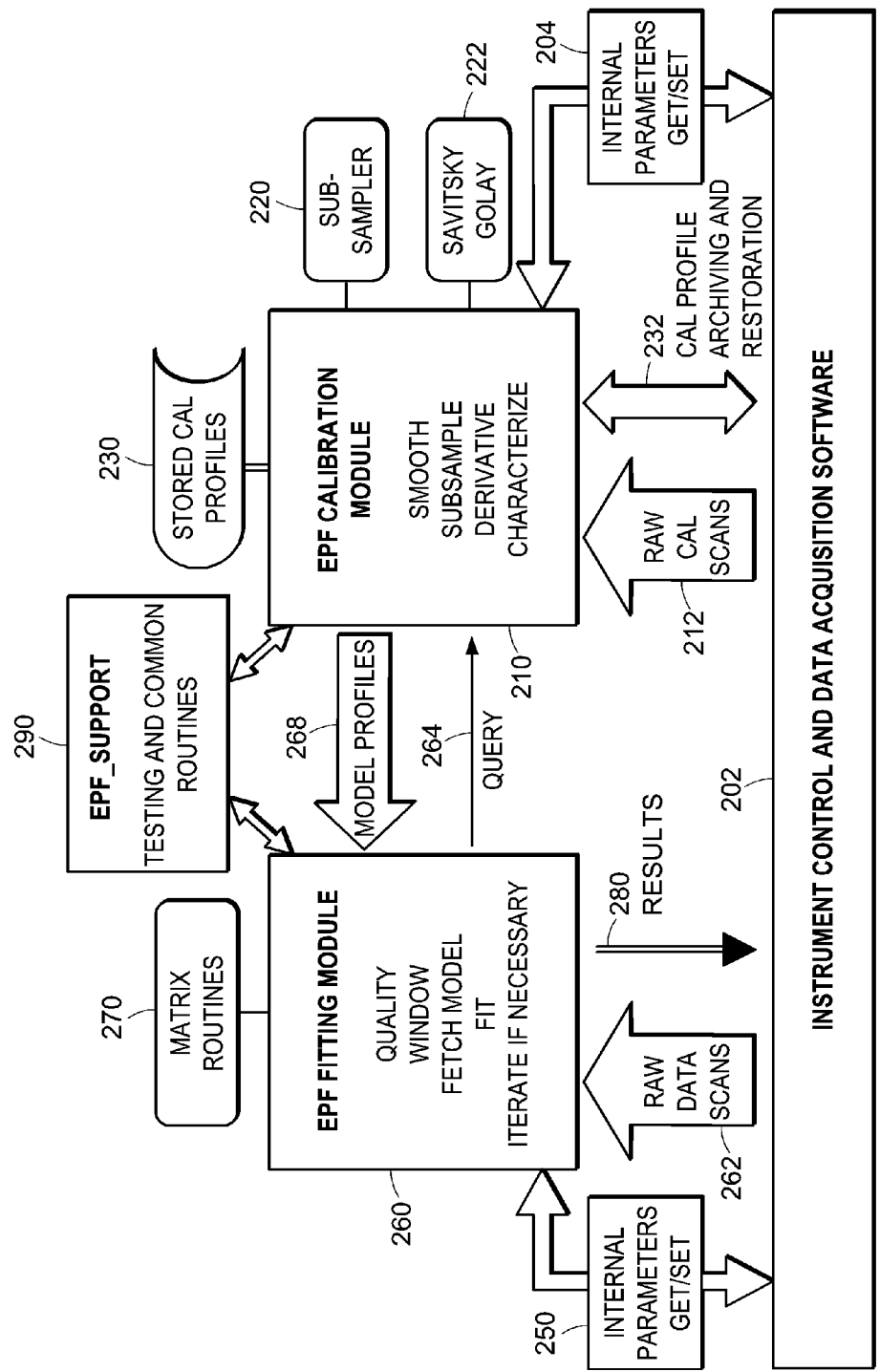
FIG. 2 is a block diagram of an example implementation of the apparatus for quantitating surface-binding optical resonance profiles of the present invention.

FIG. 2 depicts a block diagram of a preferred embodiment of the EPF calibration and fitting system, including links to the instrument control software. As seen in FIG. 2, the Instrument Control and Data Acquisition Software 202 is utilized to get and set internal parameters 204 in the EPF Calibration module 210. In this embodiment, raw data 212 from a calibration scan is sent from the Instrument Control and Data Acquisition Software 202 to the EPF Calibration module 210, which funnels the data through a Subsampler 220 and a Savitsky-Golay smoothing routine 222 before taking derivatives and characterizing the data to create a model calibration profile for each ROI being scanned. The model calibration profiles are then optionally stored 230 for later optional archiving and restoration 232 under the control of the Instrument Control and Data Acquisition Software 202.

Next, the Instrument Control and Data Acquisition Software 202 is utilized to get and set internal parameters 250 in the EPF Fitting module 260. Raw data 262 from a run-time scan for one ROI performed utilizing the chip is sent from the Instrument Control and Data Acquisition Software 202 to the EPF Fitting module 260, which qualifies it, queries 264 the EPF Calibration module 210 for the model profile 268 for the chip, and then fits the curve utilizing various matrix routines 270, iterating the process when necessary. Results 280 from the fitting process are then returned to the Instrument Control and Data Acquisition Software 202, which then provides them to the user. In the preferred embodiment, the EPF Support module 290 interacts with both the EPF Calibration module 210 and the EPF Fitting module 260 to provide various testing and common routines.

Figure 3:
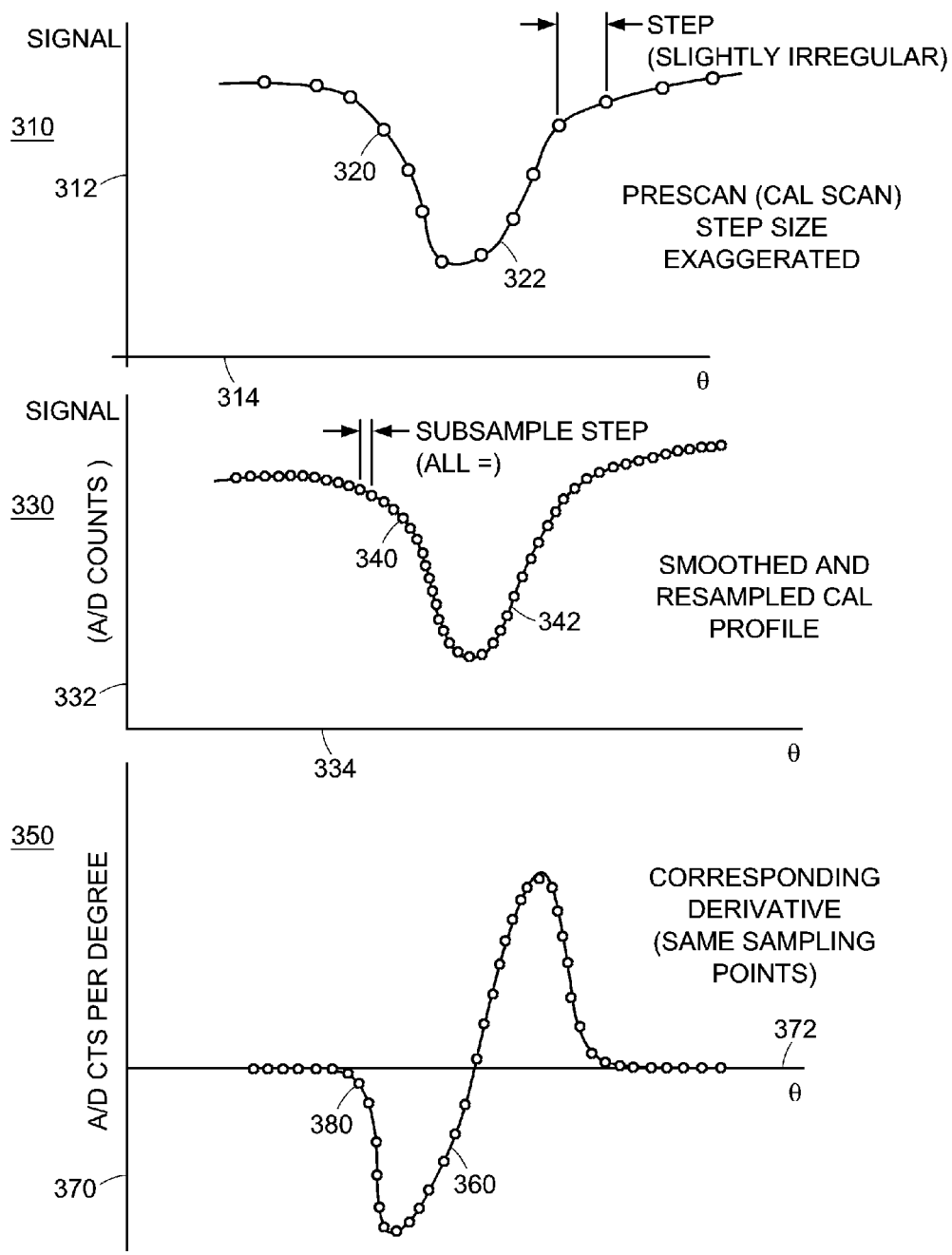
FIG. 3 is a diagram illustrating the graphical output of a calibration scan according to the present invention.

FIG. 3 depicts the graphical output of a calibration scan according to the present invention. As seen in FIG. 3, the raw calibration scan (prescan) data for ROI #n are plotted on graph 310 as signal strength in A/D counts 312 versus incidence angle $\theta$ 314. Each circle 320 represents an actual scan data point. The step-size, as well as its variability, is exaggerated so that it can be seen that the distances between steps are slightly irregular. A continuous curve 322 is drawn through the data points 320 in order to guide the eye, but plays no role in the actual analysis.

In FIG. 3, graph 330 shows the result of smoothing and resampling of the initial profile curve for ROI #n, again plotted as signal A/D counts 332 versus incidence angle $\theta$ 334. The subsampled steps represented by sampling points 340 are all now equidistant apart, allowing the production of smoothed and resampled calibration profile 342. Graph 350 shows the corresponding derivative curve 360, plotted as A/D counts per degree 370 versus incidence angle $\theta$ 372. The data points 380 are the same as sampling points 340 in graph 330.

Figure 4:
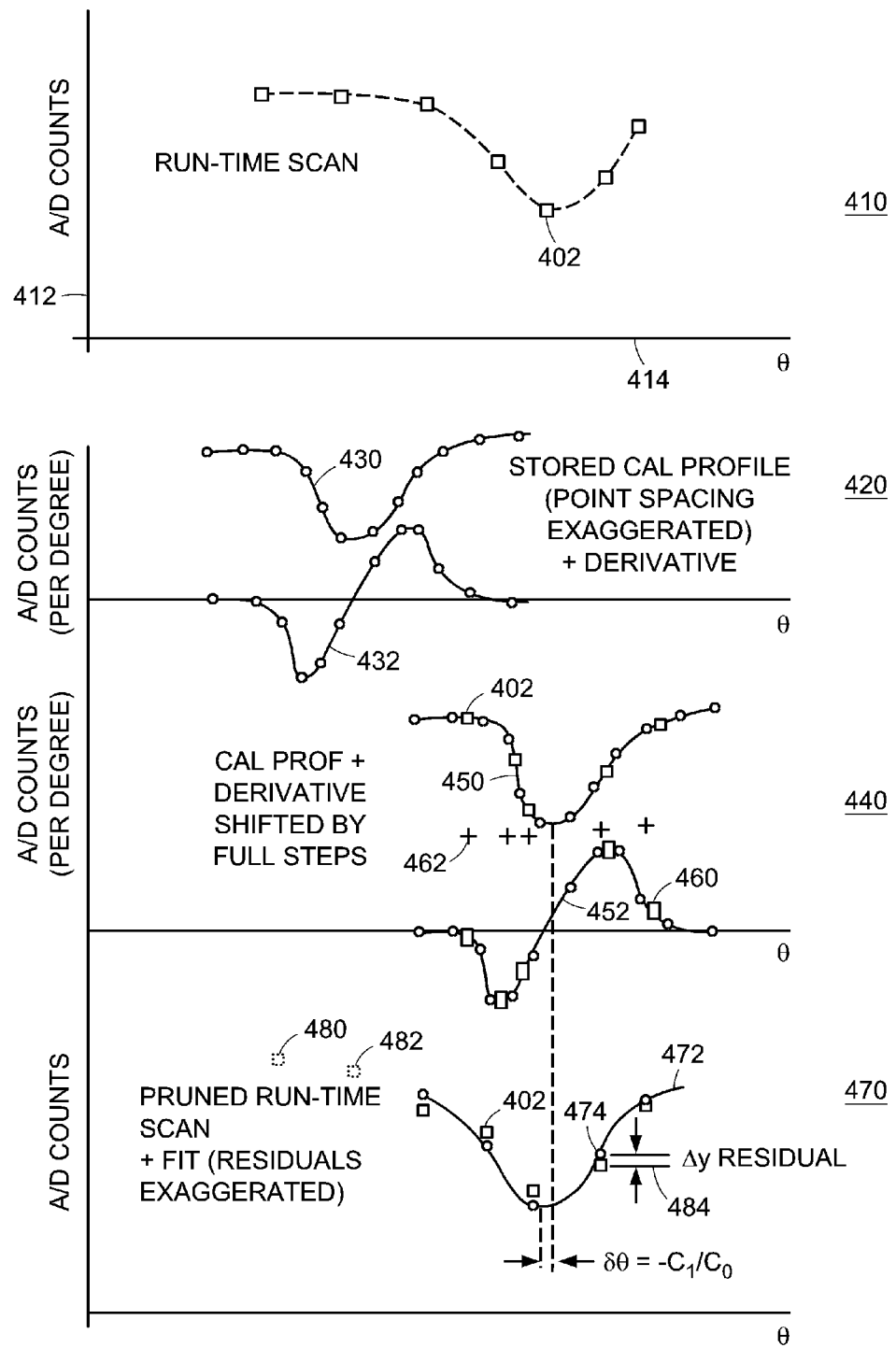
FIG. 4 is a diagram illustrating the graphical output of a run-time scan according to the present invention.

FIG. 4 depicts the graphical output of a run-time scan according to the present invention. As seen in FIG. 4, data points 402 obtained during a run-time scan of ROI #n are plotted on graph 410 as A/D counts 412 versus incidence angle $\theta$ 414. The angle steps at which data points 402 are obtained may be, and frequently will be, irregular. Graph 420 shows the stored calibration profile 430 and derivative 432 being used to fit ROI #n on the same scale used for graph 410. The profile 430 is preferably also from ROI #n, but may be from another ROI if desired.

In FIG. 4, graph 440 shows the calibration profile 430 shifted by full steps until it can be fitted to the run-time scan data points 402, resulting in curve $y_{shft}$ 450. Derivative curve 432 is similarly shifted to produce derivative curve 452 and the run-time angle points 460 located. Flat baseline model component 462 is also shown. The derived empirical profile is shown in graph 470. The raw data points 402 are shown as squares and the points 474 from the shifted calibration curve $y_{shft}$ 450, here available at fine angle spacing (0.01 degree), are shown as circles. The empirical profile is limited to a selected fitting window that does not include pruned raw scan points 480, 482. The raw data points 402 are fitted with a model consisting of shifted profile $y_{shft}$ 450, derivative term 452 (shown sampled at the data point separation), and a baseline offset (not shown.) Solid line y 472 is the resulting empirical profile, essentially a smoothed and shifted version of actual calibration profile 430, which may be from the same ROI or another. In graph 470, the residuals are exaggerated for emphasis.

Calibration Stage. In the preferred embodiment of the present invention, to begin the Calibration stage an SPR scan is performed on an SPR chip at relatively high angular point density, typically 0.05° nominal point spacing, and over sufficient angular range to encompass the full SPR resonance profiles at all ROIs on the chip. The full two-dimensional data set obtained is then transmitted to the calibration routine along with a vector providing actual measured encoder angles for each angle point. It is not necessary that the angle steps be exactly uniform.

Once there, the individual ROI scans are handled individually. Each is extracted from the 2-dimensional array and, in the preferred embodiment, is prechecked for quality. Each must actually have a resonance dip of adequate depth, must have a minimum peak intensity (outside the dip), and must have only one major dip. Angles must be monotonically increasing. Once qualified as usable, the resonance is subsampled to a higher angular density, with rigidly standardized angular point spacing, typically 0.010°. In the preferred embodiment, this subsampling is carried out by a series of steps as follows:

1. Raw scans are optionally presmoothed using Savitsky-Golay or any other suitable smoothing technique.

2. The quasi-randomly spaced points are interpolated using any suitable interpolation method, such as cubic spline or Lagrange, in order to determine subsampled points on the desired regular angle grid. If desired, this step can be avoided or reduced to simple linear interpolation by use of a very fine calibration step size.

3. The ends of the scan are then optionally extrapolated slightly using polynomial fits to the end portions of the scan in order to increase the range slightly to permit further filtering without loss of scan range.

4. The interpolated, extended scan is then optionally smoothed for a second time, using Savitsky-Golay or another suitable smoothing technique. The Savitsky-Golay or other smoothing parameters for each stage are adjustable.

The regularized, subsampled profiles are then optionally examined to determine certain properties, which are checked against control limits to establish the acceptability of each ROI profile. In the preferred embodiment, the properties measured include:

1. Nominal Resonance Angle, determined by finding the analytic minimum of a polynomial fit to the bottom portion of the resonance. The value obtained varies according to the polynomial order used and the point selection, but the absolute value is not important. Without this property, only angle shifts can be reported, not actual angle values.

2. Nominal width, expressed at Full Width at Half Maximum (FWHM).

3. Nominal Fractional Depth of resonance.

4. Maximum Intensity In Profile.

Other properties whose values may be useful may also be measured. These results are then used to establish an overall quality index for each profile. In a typical embodiment, the quality ratings are values such as "Excellent", "Good", "OK", "Poor but usable", and/or "Bad." Anything similar is, of course, suitable for use in the present invention.

The subsampled and regularized profiles for each ROI are inserted into a two-dimensional array, which may optionally be archived for later use, along with the associated property values, particularly including the nominal resonance angle. The original angle set used for the profile measurements is generally no longer needed and may now be discarded, unless a future use for it has been identified in a particular embodiment of the invention.

Finally, derivative vectors are computed for each of the profiles. In the preferred embodiment, this is accomplished using a Savitsky-Golay first derivative filter, but other methods known in the art would also be suitable. Specific parameters are adjustable, but an order of 3 and a Number Of Points of 9 are typically used. The derivatives are also combined into a 2-dimensional array for storage in memory. These are not typically archived, as they can be easily recomputed when archived subsampled profile sets are retrieved, but they may be archived if the need arises.

Figure 5:
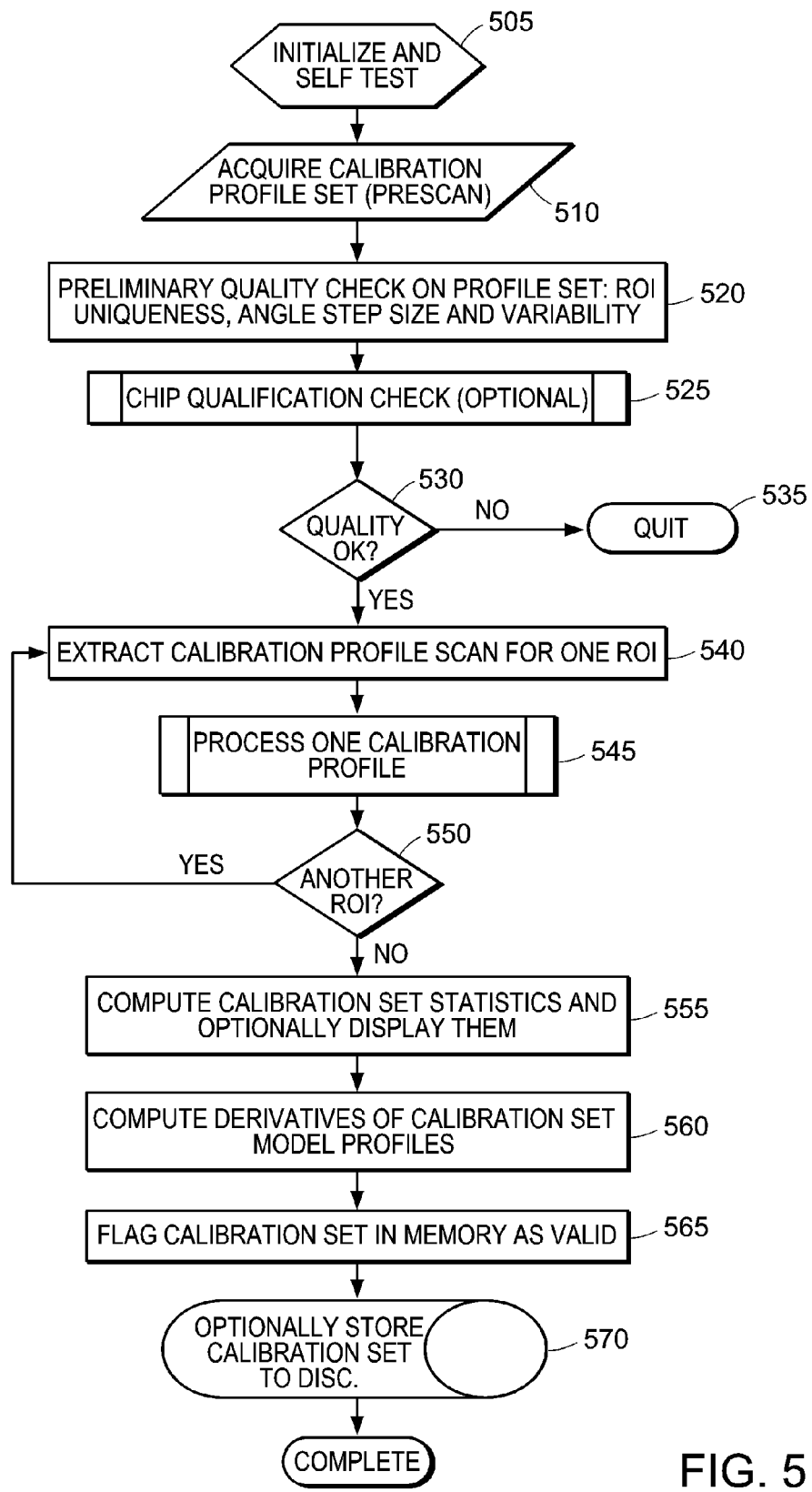
FIG. 5 is an operational flowchart of the calibration stage of the present invention.

FIG. 5 is an operational flowchart of the Calibration stage of the preferred embodiment of the present invention. Each of the steps is described in more detail in the text that follows. A description of the implementation of the preferred embodiment is presented at the end of the Detailed Description section.

As seen in FIG. 5, in the preferred embodiment the Calibration stage begins with an initialize and self-test procedure 505. The prescan SPR scan is performed on the chip being profiled in order to acquire the calibration profile data set 510, which is then subjected to a preliminary quality check 520. If desired, the optional chip qualification check 525 may be performed at this point. If the quality is not acceptable 530, the process is halted 535 and the user is informed of the problems discovered. Otherwise, a calibration profile is extracted 540 and processed 545 for the first ROI. If there are other ROIs to be profiled 550, steps 540 and 545 are repeated. Otherwise, Calibration set statistics are computed 555 and optionally displayed to the user. Next, derivatives of the calibration set model profiles are computed 560 and the calibration set is flagged as valid in memory 565. The calibration set may next be optionally stored in memory 570.

Initialize and Self-Test 505. In the preferred embodiment, the detailed operation of the EPF calibration software is controlled by a set of control parameters. Default values of these parameters are contained within the program and are set by the calibration initialization routine. Optionally, the control software may retrieve the current parameter set and/or set new values. The calibration initialization procedure also initiates a complete test of the EPF calibration module from end-to-end, using test procedures that employ randomized synthetic data. The test results are then verified for correctness. In the preferred embodiment, the initialization process also includes setting a calibration initialization flag.

Acquire Calibration Profile set 510. The SPR signal is measured for each ROI as a function of angle of incidence over a range sufficient to encompass all resonances on the chip. Angle steps are maintained nominally equal at a predetermined value, typically 50 mDeg or approximately 5% of the width (FWHM) of the resonance. SPR signals are averaged over the detector pixels defining each ROI, which comprise typically 200 to 4000 CCD pixels each. ROI shapes may be of various shapes, including rectangular, elliptical, or annular. Signals are usually expressed in mean A/D (Analog to Digital) counts averaged over the ROI, but any consistent units, including, but not limited to, photons, photoelectrons, volts, or microwatts may be used. Since the detector integration time is fixed for an experiment, it does not matter whether light power (microwatts, photons/sec, etc.) or integrated flux (photons, counts, microjoules, etc.) are used. In the preferred embodiment, the full data set is contained in a two-dimensional array, with indices of ROI index and angle index. A separate vector contains the angle values, preferably angles measured using an angular encoder. Thus actual measured angles, rather than nominal commanded angles, are preferably employed.

In normal operation, these data are acquired by the instrument control software and passed immediately to the main EPF calibration routine. However, the EPF calibration routine may also be used in a post-run mode for reanalysis of data sets, in which case the raw calibration scans will have been stored and retrieved.

Preliminary Quality Check 520. Routine checks of the appropriateness of the data set are made. This step is not essential, but serves to uncover possible problems with the data set. Various procedures verify that each ROI label is unique, that the angle values are monotonically increasing, and that the individual angle step sizes are within spec. One of these routines also establishes the precise angle range and evenly spaced angle values to be used for the final calibration profile set.

Chip Qualification Check 525. In one embodiment of the invention, the SPR chip itself may optionally be tested against expected quality standards to ensure that the chip or its preparation is not defective. This optional aspect of the invention is described in additional detail below, in conjunction with the description of FIG. 12.

Extract Calibration Profile Scan 540. In the preferred embodiment, a vector extraction routine copies one ROI scan from the array for detailed processing.

Process one Calibration Profile (core procedure) 545. This procedure is described in more detail later, in conjunction with the description of FIG. 6.

Compute Calibration Set Statistics 555. In the preferred embodiment of the invention, certain global statistics are computed, including the mean, minimum and maximum values of the following properties: estimated angles of SPR resonance minima (Nominal Resonance Angle), approximate FWHM of resonances (FWHM), peak intensity in calibration profile (Maximum Intensity), and fractional depth from upper tangent line (Fractional Depth). The global statistics can be retrieved, but are not essential in routine operation.

Compute Derivatives of Calibration Set Model Profiles 560. In the preferred embodiment, derivatives of the finished profiles are computed by using the Savitsky-Golay method, with parameters derivative order and derivative number of points typically set to 3 and 9 respectively.

Optionally store Calibration Set to disc 570. The finished calibration set may optionally be archived by the Instrument Control Software for later retrieval and use. In the preferred embodiment, derivatives are not archived as part of the finished calibration set, but are recalculated when needed. Alternatively, the raw calibration scans can be stored and used to recompute the calibration from scratch at a later time.

Figure 6:
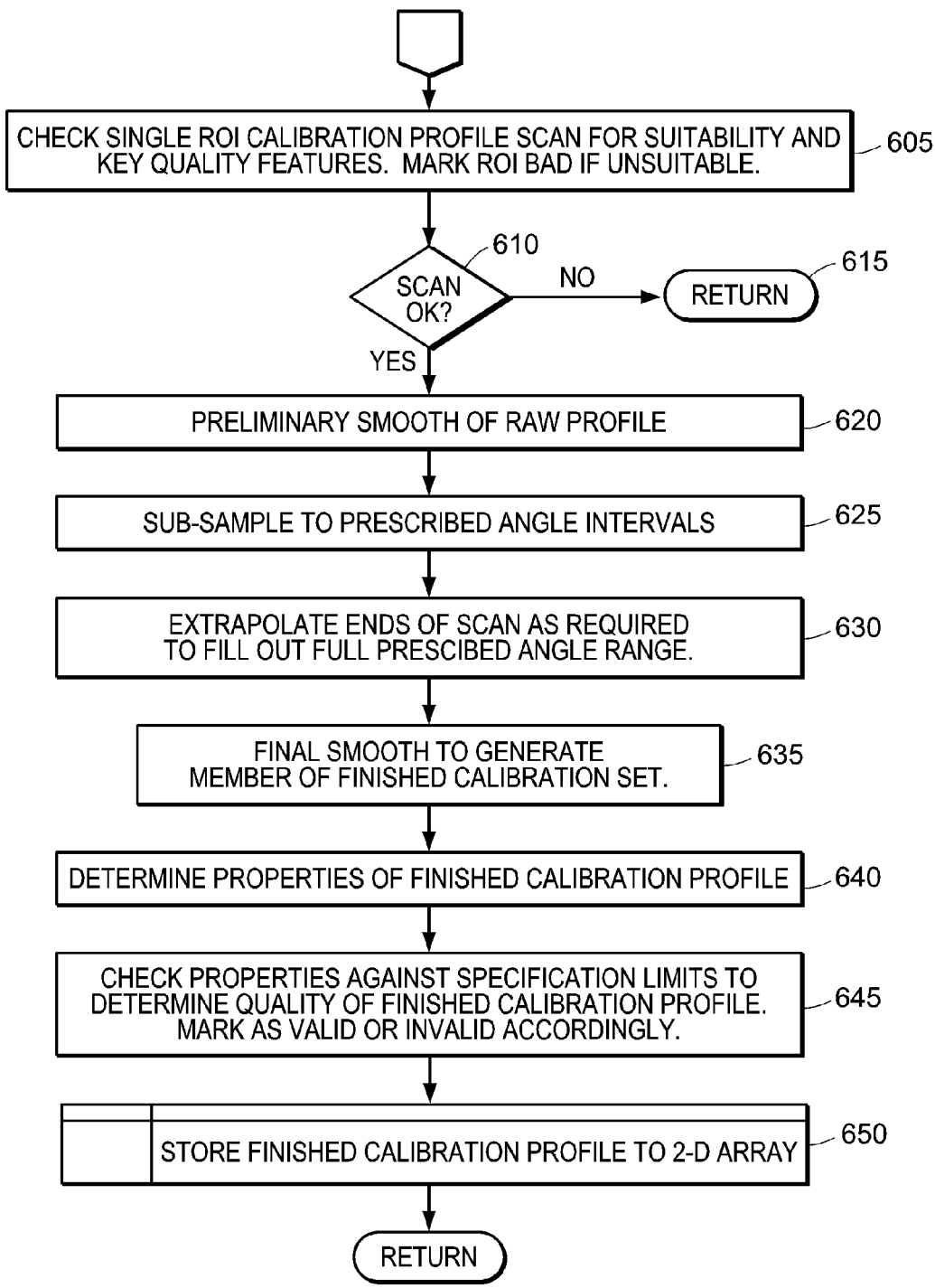
FIG. 6 is an operational flowchart of the processing of a calibration profile.

FIG. 6 is an operational flowchart of the processing of a single ROI calibration profile, shown as step 545 in FIG. 5. Each of the steps is described in more detail in the text that follows. A description of the implementation of the preferred embodiment is presented at the end of the Detailed Description section.

As seen in FIG. 6, the selected ROI calibration scan is checked for suitability and key quality features 605. If the scan is found to be unsuitable 610, the ROI is returned as "Bad" 615. Otherwise, a preliminary smooth is performed 620 on the raw profile data, and the resulting curve is subsampled 625 to prescribed angle intervals. The ends of the scan are then extrapolated 630 as required to fill out the prescribed angle range and a final smooth 635 is performed to generate a member of the finished calibration data set. Next, various properties of the finished calibration profile are determined 640 and checked against specification limits to determine the quality 645 of the finished calibration profile. Finally, the finished profile is stored 650 to a 2-dimensional array.

Check single ROI Calibration profile scan for suitability 605. In the preferred embodiment, a simple set of rough suitability tests is performed on the current raw scan. These include, but are not limited to, checking for a sufficient number of data points, checking the peak and minimum signals in the scan against specification limits, testing the ratio of minimum signal to peak signal against the maximum limit in order to preliminarily verify an adequate resonance depth, finding the angle step at which the minimum signal occurs (presumed to be the approximate resonance position), and checking for adequate scan range on either side of this minimum.

In the preferred embodiment, an additional test is made to ensure against multiple deep dips that could cause ambiguity in the resonance determination. Failure of any of these tests causes the ROI profile property to be flagged "Bad", a reason why the profile is bad to be determined, and further processing of this ROI to be terminated. Warning levels of these quantities will cause the ROI to be flagged "Poor", but processing will continue. Failure of any one ROI scan does not prevent successful processing of other ROI scans.

Preliminary Smooth 620. In the preferred embodiment, actual preliminary smoothing is carried out by the conventional Savitsky-Golay smoothing method. The implementation used in the preferred embodiment, unlike some Savitsky-Golay implementations, does not truncate the length of the scan. This is preferably a relatively gentle smooth, with parameters 2, 3. This smoothing operation may be omitted entirely on clean data without compromising the overall process. Other suitable smoothing methods known in the art may be similarly utilized.

Subsample to prescribed angle intervals 625. In the preferred embodiment, the scan is then resampled to the earlier defined angle steps using an interpolation procedure. Although Lagrange interpolation may be advantageously used, Cubic Spline interpolation performs adequately, and this is employed in the currently preferred embodiment. Any other method known in the art would also be suitable. The subsampled step intervals are a prescribed subdivision, typically 5, of the nominal angle step size (typically 50 mDeg).

Extrapolate ends of scan 630. In some cases, the end points of the final angle range for the calibration set are set to be slightly beyond the minimum and/or maximum angles actually measured. In such cases, the end points must be extrapolated. The cubic splines determined in the previous step are unsuited for extrapolation, so, in the preferred embodiment, a separate polynomial fitting procedure is used on one or both ends of the scan, as needed. A polynomial of order n is fitted to the final n+1 resampled points determined previously, and this polynomial is evaluated at the missing angle values (usually no more than one) to carry out the extrapolation. Use of this procedure assures that the range of the calibration profile is not unnecessarily reduced by truncation due to the inevitable mismatch of experimental angle values and the regularized angle steps. Any other suitable extrapolation techniques known in the art may also be advantageously utilized for this step.

Final Smooth 635. In the preferred embodiment, the smoothing procedure is used again to perform a non-truncating final smooth of the resampled profile, with parameters order and number of points typically being 3 and 9.

Determine Properties of finished calibration profile 640. In the preferred embodiment, the detailed properties of the final resampled profile are determined by a separate property determination procedure. Properties determined may include, but are not limited to, FWHM, Nominal Resonance Angle, Fractional Depth, and Maximum Intensity. Aside from the Nominal Resonance Angle, these properties are currently used only for assessing system performance, and for estimating the quality of the calibration profiles.

Check Properties against specification limits 645. In the preferred embodiment, the properties Maximum Intensity, Nominal FWHM, and Nominal Fractional Depth are checked against specification limits, and the profile quality is set accordingly to appropriate quality labels such as "Excellent", "Good", "Poor", or "Bad".

Store Finished Calibration Profile 650. In the preferred embodiment, the completed resampled, smoothed and qualified profile is saved to a persistent internal data structure.

The Profile Properties returned by the calibration routines are defined in special ways. The definitions may best be understood with reference to FIG. 7, a diagram depicting the definitions of the profile properties returned by epfCal in the preferred embodiment of the invention. Calculations are carried out on the subsampled profile 702, not on the raw data indicated by the diamond symbols 705.

Figure 7:
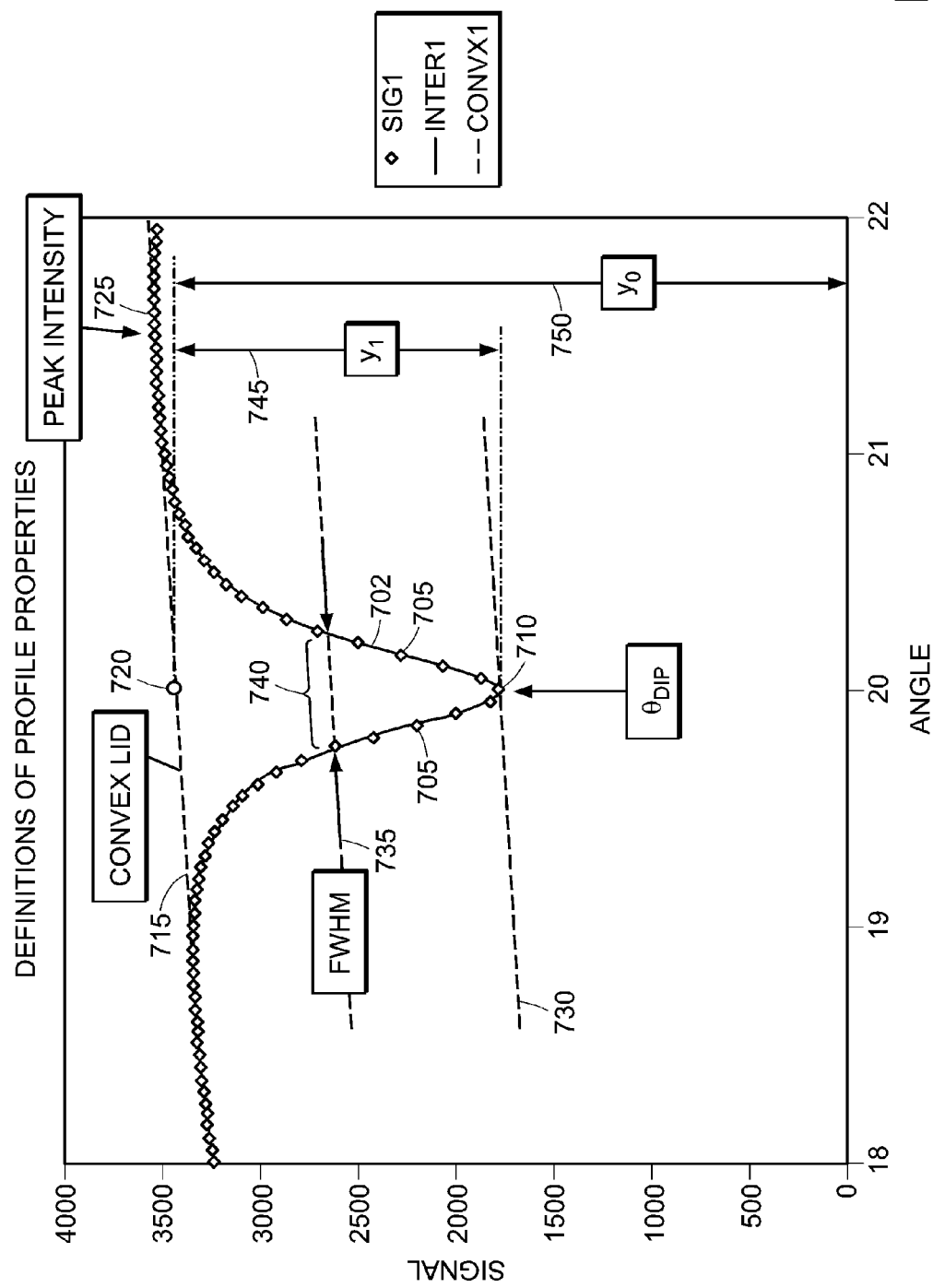
FIG. 7 is a diagram depicting the definitions of the profile properties returned during the calibration stage of the present invention.

First, the minimum 710 of the curve 702 is identified and is denoted $\theta_{DIP}$. In the preferred embodiment of the invention, this Nominal Resonance Angle 710 (SPR "minimum") is located by a polynomial fit to the bottom region of the subsampled profile. Next, the line tangent to the profile 702 from above, called the convex lid 715, is determined in order to assist in the estimation of the width and depth of the resonance in the presence of a curved baseline. Computations of width and fractional depth are carried out on the residuals obtained by subtracting the profile 702 from the convex lid 715. The point 720 shown on the convex lid is directly above the SPR minimum 710 and is used to estimate the fractional depth. As shown in FIG. 7, the Peak Intensity 725 in the profile 710 is the highest subsampled point.

A line 730, parallel to the convex lid 715, is drawn through the minimum point 710, and another parallel 735 is drawn midway between the convex lid and the parallel through the minimum. The full width at half maximum 740 (FWHM) of the profile is the angular spread between the intersections of the midway parallel 735 and the side of the resonance profile 702. No attempt is made to interpolate between subsampled points, so this value is rounded to the subsampling angle interval.

The fractional depth of the SPR is taken as $y_1/y_0$, where $y_1$ 745 and $y_0$ 750 are as shown in the figure. Again, no attempt is made to interpolate between subsampled points, so this value is slightly approximated.

Properties determined are therefore:

a) Peak Signal in scan 725.

b) Nominal Resonance Angle in degrees 710. In the preferred embodiment, this is determined by fitting a polynomial of specified order to the bottom of the resonance dip over a specified angle range. Although not fundamentally meaningful, this value can be used later to assign self-consistent absolute dip angles to fitted scans.

c) The approximate Full Width at Half Maximum (FWHM) of the resonance in degrees 740. In the preferred embodiment, to determine the approximate FWHM, a procedure effectively passes a line through the resonance minimum that is parallel to the convex lid. It then finds the points in the profile on either side of the resonance that come closest to midway between the upper and lower lines. The angular distance between these two profile points is taken as the FWHM. Interpolation is not performed.

d) The Fractional Depth of the resonance. In the preferred embodiment, the point on this line directly above the minimum in the resonance is calculated as an estimate of the signal intensity $I_O$ in the absence of the resonance. The Fractional Depth is then determined as the ratio $(I_O - I_{MIN})/I_O$, where $I_{MIN}$ is the intensity at the resonance minimum.

Figure 8:
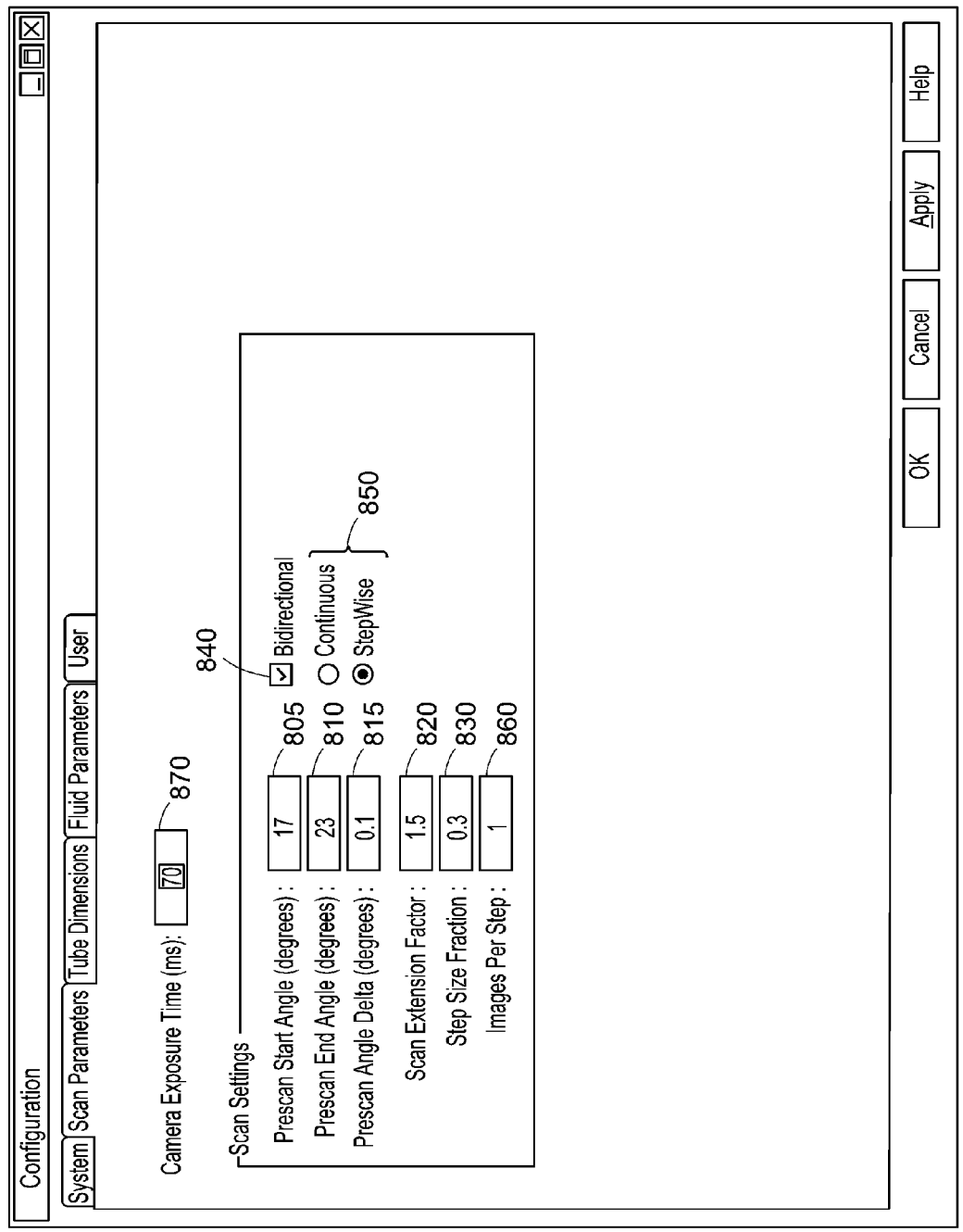
FIG. 8 is a screenshot depicting an example user interface for the initiation of the calibration stage.

FIG. 8 is a screenshot depicting an example user interface for the configuration and initiation of the calibration stage. The same screen is also used for the configuration and initiation of the Fitting stage. It must be appreciated that the screen embodiment depicted in FIG. 8 is provided by way of example only and that additional parameters may be added, parameters may be deleted, or alternate screen configurations may be employed without departing from the concept of the invention.

The example configuration screen shown in FIG. 8 is used to set up various angle scan parameters. As seen in FIG. 8, the following parameters may be specified and/or verified by the user using the example screen:

a) Prescan angle range (this is the Calibration profile scan)—"Prescan Start Angle" 805, "Prescan End Angle" 810 b) Prescan angle step size —"Prescan Angle Delta" 815 c) Scan Extension Factor 820: This is the way the run-time scan range is specified in the currently preferred embodiment. The average width FWHM of the profiles determined in the calibration run is multiplied by this factor to determine the Half-range of the run-time scans. For example, if the mean FWHM is 0.8 degree, and the Scan Extension Factor is 1.5, then scans will extend 1.5×0.8=1.2 degrees above the highest observed ROI resonance, and 1.2 degrees below the lowest observed ROI resonance. This scan range may be fixed for the duration of the run, or may be adaptive, the scan limits automatically increasing or decreasing as the resonances are observed to move about under the influence of refractive index changes and chemical binding.

d) Step Size Fraction 830: This is a factor that currently determines the run-time scan angle step size. In the preferred embodiment, rather than specifying it directly, it is calculated as a fraction of the mean FWHM. It may alternatively be specified in degrees, or in any other suitable manner known in the art.

e) The Bi-Directional checkbox 840, if checked, causes data to be acquired as the instrument's light source scans both up and down in angle, thereby saving the time otherwise required to mechanically slew back to the beginning for each scan. Use of this mode requires that the Time—of resonance feature of the EPF be employed, since otherwise large alternation in the time intervals between resonance measurements on successive scans results when the resonances are not exactly at midscan.

f) Continuous vs. Stepwise 850: The preferred embodiment of the system supports either or both stepwise start-stop angle scanning or a non-stop measure-on-the-fly mode.

g) Images per Step 860: In stepwise scanning, a variable number of CCD exposures (frames) may be measured at each step. Usually one image is obtained per step, but additional images may be co-added to improve signal-to-noise h) Camera Exposure Time 870: The exposure time for each CCD frame is chosen to use as much of the CCD pixel well capacity as possible, while avoiding any risk of saturation on individual pixels. It depends entirely on the LED light source intensity, but is typically 25-100 ms.

It should be understood that this and other types of configuration screens may be expanded to include any other suitable calibration and/or fit parameter settings.

Figure 9:
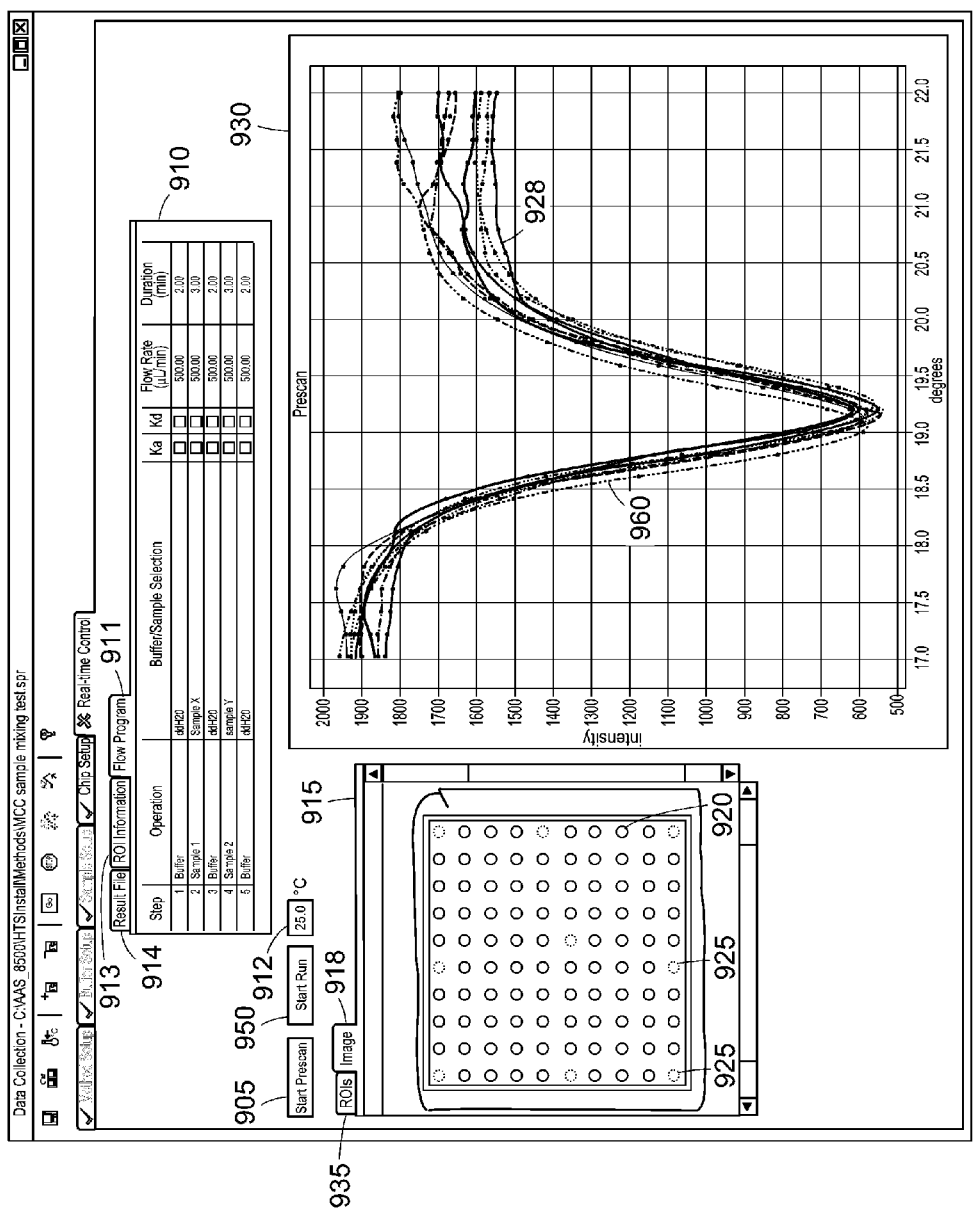
FIG. 9 is a screenshot depicting an example output from the calibration stage.

FIG. 9 is a screenshot depicting an example output from the calibration stage. It must be appreciated that the screen embodiment depicted in FIG. 9 is provided by way of example only and that additional parameters or graphics may be added, parameters or graphics may be deleted, or alternate screen configurations may be employed without departing from the invention. In the preferred embodiment, this screen is visible while performing the Calibration Profile Scan, being updated as each ROI is analyzed.

As shown in FIG. 9, the button 905 that initiates a calibration scan is shown on the left. Visible at the top of the screen is a listing of the run method 910, selected by clicking on the "Flow Program" tab 911, showing the sequence of fluidic control steps which occur during the run and which influence the reaction sequence giving rise to the SPR signal. The run temperature (temperature of the chamber containing the sample and SPR chip) is shown in box 912. Alternate information display choices may be had by selection of the "ROI Information" tab 913 or the "Result file" tab 914. On the left is an image 915 of the SPR chip itself, brought onto the screen by clicking the Image tab 918, showing the locations of active ROI zones 920. Several of the ROIs are highlighted 925; these highlighted ROIs are the ones for which angle scans 928 are displayed in the large graph 930 at the lower right. An alternative to the Image tab 918 is the ROIs tab 935, in which the locations of the ROIs are displayed graphically, but without an actual monochrome chip image. In one embodiment, a similar screen is used to display the results of the run-time scan, initiated by clicking the Start Run button 950.

In the preferred embodiment of the invention, during the calibration scan, which takes a few seconds, the graph 930 is updated in real time. The actual measured intensities, averaged over ROI pixels, are the dot symbols 960 on the plot. The lines 928 between them are interpolated for cosmetic purposes using standard graphic smoothing functions, such as, but not limited to, splines or bezier curves. Note that the ROIs displayed in FIG. 9 exhibit some variation in shape, especially in the wings, as well as some dispersion in angular position. This is normal. These, and the rest of the similar curves for the other ROIs, are the grist for the calibration mill. In the preferred embodiment, the intensity for each pixel is converted by a 12-bit A/D converter to an A/D count between a range of 0 and 4096 ($2^{12}$). The angle is obtained from precision angular encoder readings.

Figure 10:
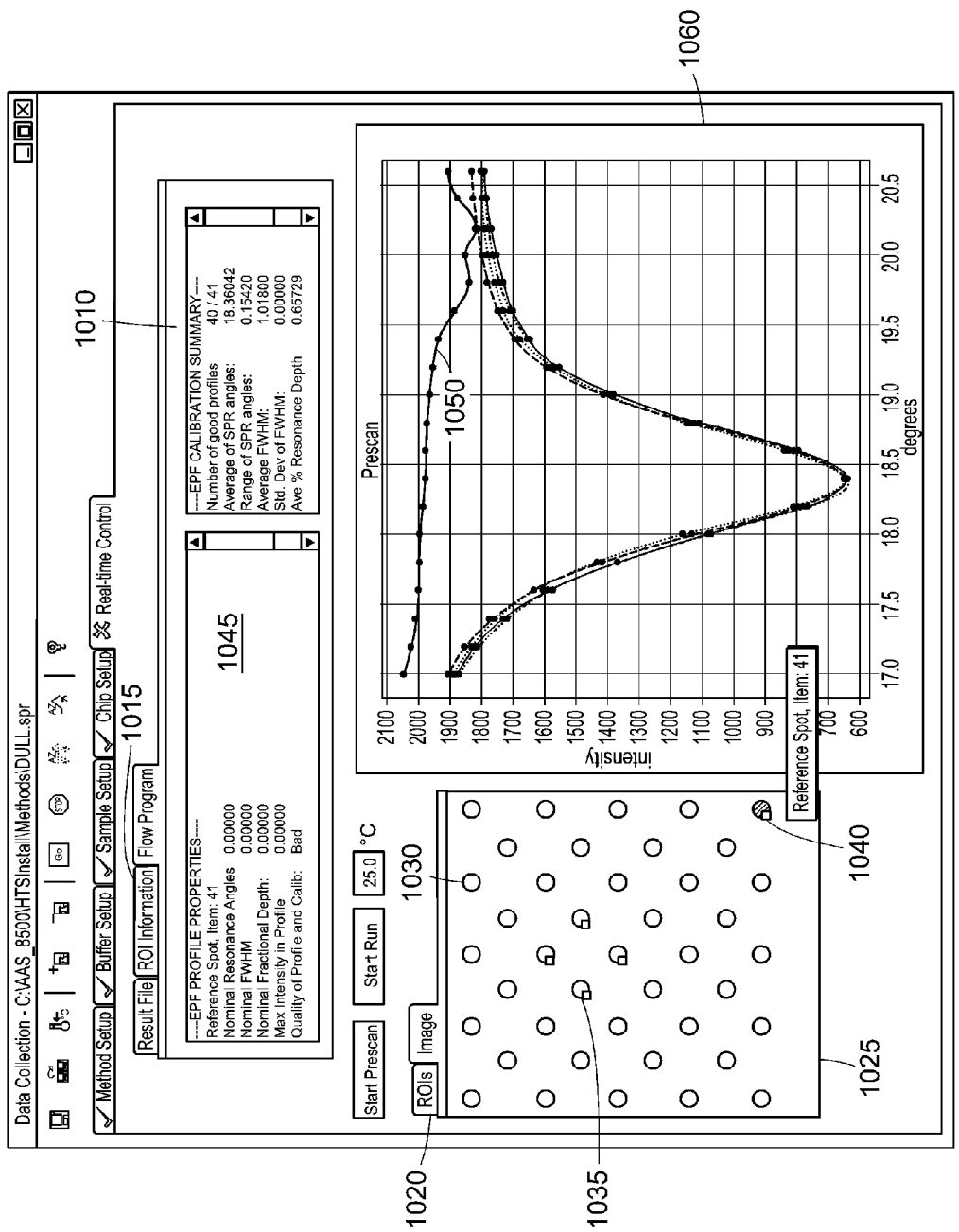
FIG. 10 is a screenshot depicting a different example output from the calibration stage, wherein there is a bad region of interest (ROI) 41 showing no resonance.

FIG. 10 is a screenshot depicting a different example output from the calibration stage, wherein there is a bad region of interest (ROI) 41 showing no resonance. It must be appreciated that the screen embodiment depicted in FIG. 10 is provided by way of example only and that additional parameters or graphics may be added, parameters or graphics may be deleted, or alternate screen configurations may be employed without departing from the invention.

As shown in FIG. 10, the EPF calibration summary 1010 is shown at upper right. It is provided when the "ROI Information" tab 1015 is selected. The ROIs tab 1020 is selected, so the chip is displayed in the graph 1025 at lower left as a series of spots 1030 representing the active ROIs. ROIs marked with squares 1035 are selected for plotting in the chart pane at right. The selected ROI 1040 (ROI 41) is "bad", showing no resonance, as can be seen in the EPF Profile Properties window 1045 and in the resonance curve 1050 in the large graph 1060 at lower right.

Figure 11:
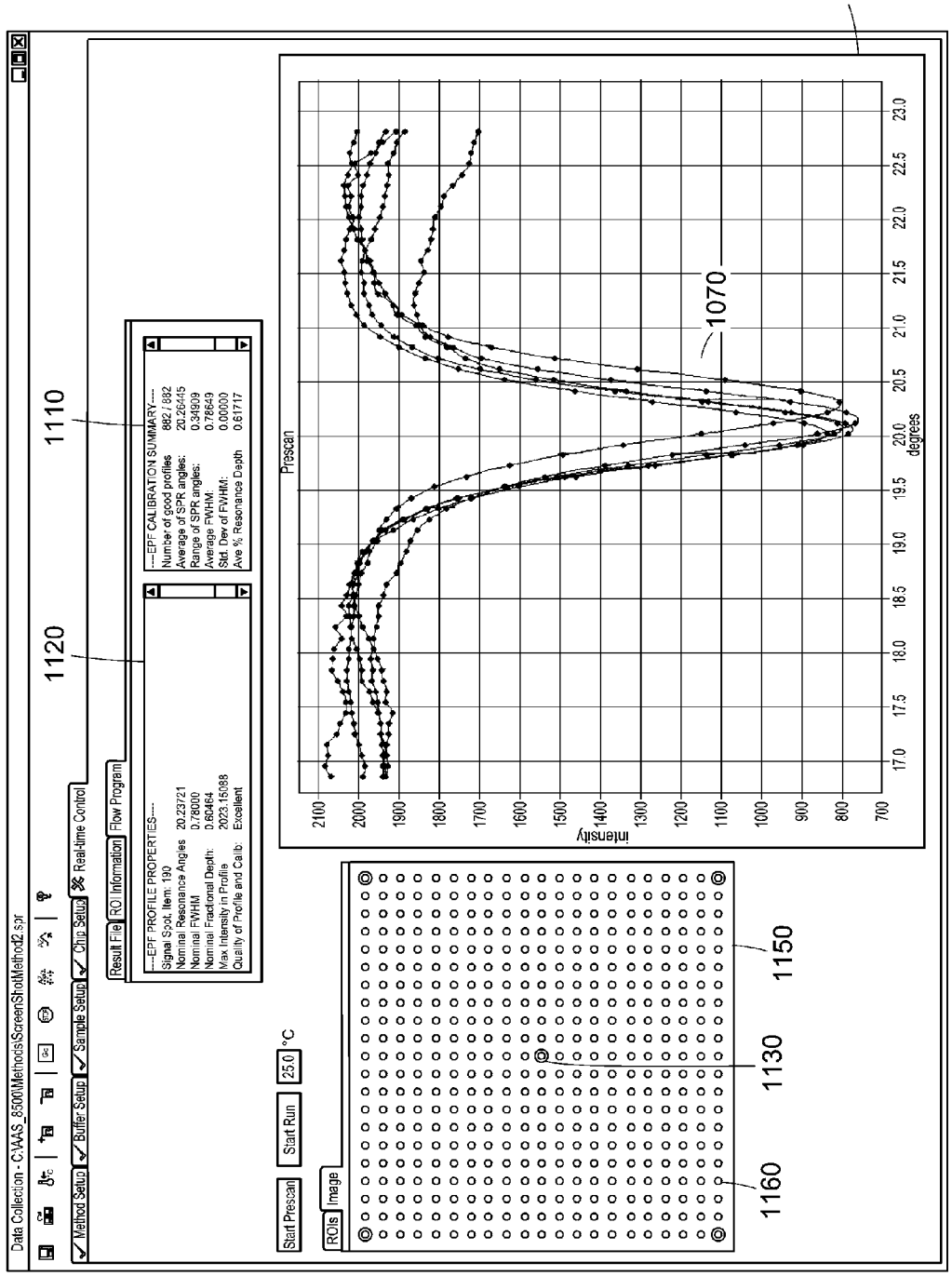
FIG. 11 is a screenshot depicting yet another example output from the calibration stage, showing the details of "good ROI" 190.

FIG. 11 is a screenshot depicting a different example output from the calibration stage, showing the details of "good ROI" 190. Again, it must be appreciated that the screen embodiment depicted in FIG. 11 is provided by way of example only and that additional parameters or graphics may be added, parameters or graphics may be deleted, or alternate screen configurations may be employed without departing from the invention.

As shown in FIG. 11, the EPF calibration summary 1110 is shown at upper right and the EPF Profile Properties 1120 of selected ROI 190 1030 are shown at upper left. The ROI tab 1140 is selected, so the chip is again displayed in the graph 1150 at lower left as a series of spots 1160 representing the active ROIs. Several of the ROIs are highlighted; these highlighted ROIs are the ones for which profiles 1170 are optionally displayed in the large graph 1180 at the lower right.

Chip Qualification Check. The mechanisms of the EPF permit a rigorous assessment of chip quality to be made from the calibration data, before proceeding with the calibration data set generation. SPR chips of particular types or batches should have very similar SPR profiles. Any deviations from these profile shapes and angular positions are a sign that the chip was incorrectly manufactured or processed, or that it has been damaged. Valuable user time and sample material can be saved by identifying defective chips before commencement of the full run.

To implement this feature in the preferred embodiment, representative calibration profiles, averaged over several full chips of known good quality, are generated for each type or distinct batch of devices. Although these could be generated on an ROI-by-ROI basis, in general a single profile representative of the whole chip will be used. Expected and allowable variations from this "Golden Profile" will also be established. This Golden Profile data, along with the allowable variance specifications, can be shipped with the SPR chips from the factory or be otherwise distributed to the user, and then stored on the instrument control computer.

Figure 12:
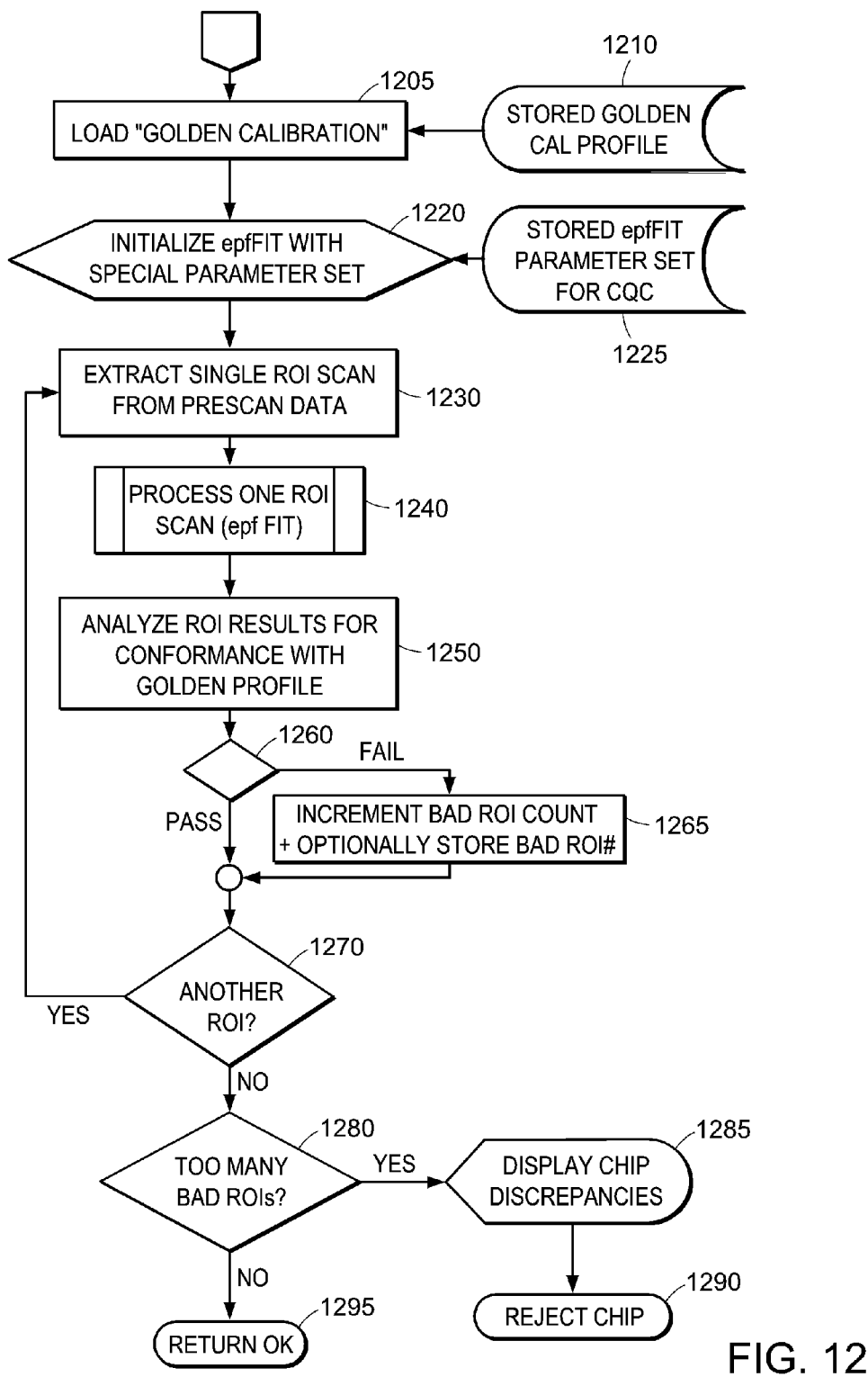
FIG. 12 is an operation flowchart for the optional chip qualification procedure.

FIG. 12 is an operation flowchart for the optional chip qualification procedure, as shown in step 525 of FIG. 5. Each of the steps is described in more detail in the text that follows. A description of the implementation of the preferred embodiment is presented at the end of the Detailed Description section.

As shown in FIG. 12, the chip qualification procedure is initiated by loading the correct "golden calibration" 1205 from among the stored golden calibration profiles 1210. Next the fit module is initialized 1220 with the stored chip qualification parameter set 1225. A single ROI scan is extracted from the calibration scan data 1230, it is processed 1240 as described below in conjunction with FIG. 14, and the results are analyzed for conformance with the golden profile 1250. If the results for that ROI fail the test 1260, the count of bad ROIs is incremented 1265 and the number of bad ROIs is optionally stored for reporting to the user. If additional ROIs remain to be tested 1270, another single ROI scan is extracted from the calibration scan data 1230, and the process repeats until all ROIs have been processed. At the end of testing, if the number of bad ROIs found exceed the predetermined threshold 1280, the discrepancies are displayed to the user 1285 and/or the chip is rejected 1290. Otherwise, the chip qualification procedure returns an indication that the tested chip is within acceptable limits 1295.

The following steps are taken to implement the Chip Qualification Check (CQC):

Load Golden Calibration. The stored Golden Calibration archive corresponding to the chip type or batch number is loaded and made to be the current calibration set. It will typically consist of a single profile, rather than a large set of profiles for each ROI.

Initialize epfFit with Special Parameter Set. The epfFit parameters used for the CQC are generally different from those used in normal analysis operations. In particular, the specification limits for the various parameters will vary, some being tighter than normal, and others being looser. In particular, the allowed rms Residuals will be larger, since the individual ROI scans are being compared to a single standard profile rather than to individualized ROI calibrations measured on the same ROI of the same chip.

Extract single ROI scan from Prescan Data. The same calibration data set that is to be used for the calibration stage is used for the CQC. One ROI at a time is extracted from that set and submitted to the specially configured epfFit procedure. Note that the data point spacing is that of the calibration scan, and is therefore smaller than the spacing typically used for run-time scans.

Process one ROI Scan. This is identical to the process used for fitting ordinary run-time data, with two exceptions:

a) The epfFit parameters are modified, as discussed above.

b) The Calibration Profile to be associated with each ROI is different. Instead of using the recently measured Calibration Profile for the ROI in question, the Golden Profile is used for all ROIs. In the preferred embodiment, the ROI to Use is one of the calling parameters in epfFit. In this case, the value is "Golden Profile", or whatever label has been used for the Golden Profile.

Analyze ROI Results for Conformance with Golden Profile. The normal fitting process, with the modified specification limits, generates a number of quality checks in itself. The rms Residual value is the most important of these, and is therefore the primary test criterion, as it detects any significant change of shape of the SPR profiles from the expected standard shape, including changes in FWHM. As manufacturing and processing consistency changes, the allowed variances on this and other parameters may be modified. Appropriate limits on the key parameters are typically established in the light of field experience, in order to avoid excessive false rejections.

However, other parameters, not usually of direct concern in normal fitting, should also be checked. These include:

a) The SPR angle shift. Since the measurement is being made prior to the run, SPR angles should vary from the golden standard because of two effects: (i) the refractive index of the buffer solution in use, and (ii) the surface treatments or ligands applied to the chip by the user. Item (i) can be explicitly allowed for, given a definition of the buffer in use. Item (ii) cannot in general be quantitatively taken into account, except that the effect of (ii) is always to increase the SPR angle. Therefore, after taking (i) into account, any negative angular shift (beyond a specified tolerance) is a sign of trouble.

b) Baseline Fit Coefficient. If the profile shape, including resonance depth, is close to that of the golden profile, then the Baseline component in the fit should be very small. Therefore, placing limits on this fit result is equivalent to ensuring that resonance depth is within allowed tolerances.

c) Profile Fit Coefficient. This value should be of order unity, but may be allowed to dip below unity in order to account for reduced signal intensity on the target instrument. The golden profiles will have been normalized to full intensity, so this fit coefficient should be allowed to exceed unity by only a small amount.

When an ROI fails one or more of these tests, it is flagged as "Bad", and the cause of the discrepancy logged. A count is kept of the number of such out-of-spec ROIs.

Test for Too Many Bad ROIs. When all the ROIs have been analyzed, the number of Bad ROIs is tested against a predetermined limit, which may be zero. If the number exceeds this limit, the chip is rejected, or, at a minimum, the user is informed and given the option of terminating the run before committing sample solution. If desired, the user may also be informed of the specific ROIs that are "Bad", in order to allow the user to decide if the affected ROIs are of particular interest in the planned experiment.

Fitting Stage. In the preferred embodiment, when resonances obtained in the course of an experiment are to be measured, the epfFit routine is called. In this case, just one profile, corresponding to a single ROI, is submitted at a time. Three vectors are submitted: the SPR intensities, the encoder angles, and the clock times for each data point, along with the ROI ID to be used in fitting.

The angles at which the profile is sampled are generally not the same as those used during calibration, nor are they necessarily spaced similarly. Typically, much sparser angle spacing is used in order to speed up measurements. Wider angular spacing has little effect on angle determination noise until a minimum number of points per FWHM of the resonance, typically three or four, is reached, whereupon coarser spacing definitely degrades angle accuracy. Shot noise (and other amplitude noise) in the data does reduce accuracy, however, and, to the extent that coarser data point spacing results in fewer total photons going into the measurement, there is a deleterious effect.

It is possible to obtain valid fits, albeit with reduced precision and accuracy, with partial scans (i.e., incomplete resonance profiles). This is useful in extending the dynamic range of effective refractive index (RI) values that can be measured.

The fitting process is more complex than the calibration process outlined above. The essential steps are:

1. Data vectors are checked for consistent array indices. Angles are checked to make sure that the scan is monotonic in angle, although either increasing or decreasing angle is acceptable.

2. The ROI designation is checked to be sure that a calibration exists for it. It is not essential that the calibration profile used for fitting belong to the same ROI, although normally it does. If for some reason this ROI was never calibrated, or the calibration failed, then another similar ROI calibration profile may be used instead with reasonable success. This is because the fit results are not extremely sensitive to profile shape, and because it is not the absolute SPR angle, but rather shifts of angle, that are of primary interest during the course of an experiment.

3. If the angles are in decreasing order, the data vectors are inverted for convenience in comparing with the calibration profiles, which are in strictly increasing angle order.

4. The rough location of the SPR minimum is determined, using a judicious combination of locating the lowest point in the scan and fitting a small number of nearby points with a low order polynomial (quadratic). If no clear minimum can be found, the procedure fails, or, in some cases, the lowest point (if at one end of the scan) is used as a first guess.

5. The correct subsampled calibration profile and derivative, previously computed in the calibration stage, are retrieved.

6. The calibration profile and derivative are shifted in full subsample steps (typically 0.01°) to bring the calibration profile nominal minimum into coincidence with the rough SPR location determined in step (4) above. This is merely an index pointer calculation.

7. The overlap portion of the SPR scan to be fitted and the calibration profile is identified. In general, the overlap is shorter than either alone, but sometimes one is contained within the other. Only this overlap portion is used.

8. Signal and derivative values at the actual SPR scan angle values are derived from the shifted calibration profile. In the preferred embodiment, this is accomplished with Lagrange interpolation, but any other suitable method known in the art may be used. This is accurate because the angle point spacing in the calibration profiles is very small.

9. The pruned portion of the SPR scan is fitted. In the preferred embodiment, this is accomplished using classical linear least squares fitting, using as model components the following:

a) The calibration profile
b) The calibration profile derivative,
c) A constant additive offset.

10. The fractional angular shift of the apparent SPR minimum from the shifted calibration profile is determined as the quotient of two of the fit coefficients obtained in step (9) above, namely the ratio of the calibration derivative fit coefficient to the calibration profile coefficient. The latter is normally approximately unity, whereas the former is typically very small. This fractional shift is added to the discrete shift applied in step (6) above, in order to provide an estimate of the actual total SPR shift relative to the SPR location at calibration.

11. If the fractional shift obtained in step (10) exceeds half a subsample step, then steps (6)-(10) are repeated (iterated) until the fractional step is equal to or less than half a subsample step. Other termination criteria may be used successfully, although the described criteria are currently preferred. Special means are provided to prevent endless jumping to and fro when the fractional shift is very close to half a step.

12. At this stage, the SPR location has been fairly well established. The user may optionally specify, however, that a limited region of the SPR scan near the resonance be used for the final fit in order to reduce errors due to artifacts in the wings of the profile. When this "Sweet Zone" fitting is used, the SPR scan is further pruned to the specified reduced width, centered as much as possible on the resonance location, and the process from step (6) to step (11) is iterated again. The reason for not pruning to the Sweet Zone the first time around is to reduce the likelihood of grossly incorrect fits by using as much data as possible. Once the correct alignment of calibration and unknown profiles has been fairly accurately determined, further refinement using pruned scans is safe, even in pathological cases such as highly truncated resonances. However, higher execution speeds may be obtained by skipping directly to the pruned fits.

13. Various quality checks are performed. In particular, at least three points must be remaining after overlap and any further pruning in order to perform valid fits. The fitting residuals are checked against both lower and upper limits.

14. In addition to the angle shift determined above, an estimate of absolute resonance angle is made by adding this shift to the previously determined Calibration Nominal SPR Minimum angle.

15. The clock time at which the minimum occurred in the scan is estimated by interpolation between the times at which the scan data points on either side of the found minimum were measured. This Time of Minimum is highly useful for more accurately assigning the SPR angle obtained to a specific clock time for use in kinetic analysis.

16. Results of the fit are returned to the calling program, along with various details such as fit coefficients and a quality estimate based on comparing these parameters with control limits.

Figure 13:
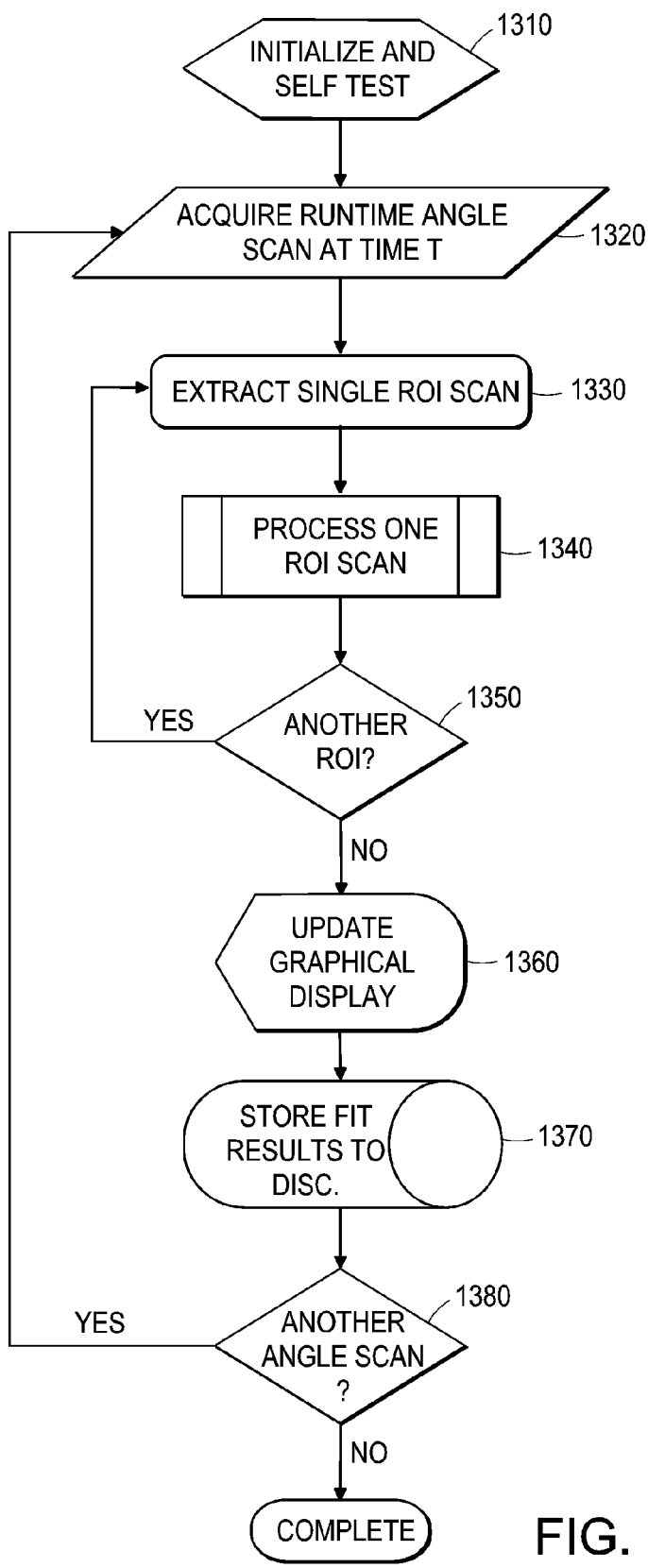
FIG. 13 is an operational flowchart of the fitting stage of the present invention.

FIG. 13 is an operational flowchart of the fitting stage of the present invention. Each of the steps is described in more detail in the text that follows. A description of the implementation of the preferred embodiment is presented at the end of the Detailed Description section.

As shown in FIG. 13, in the preferred embodiment the fit stage is begun with an initialize and self-test procedure 1310. Then the SPR run is performed and the run-time angle scan at time t is acquired 1320. Next, a single ROI scan is extracted 1330 and processed 1340 for the first ROI. If there are other ROIs to be profiled 1350, steps 1330 and 1340 are repeated. Otherwise, the graphical display is updated 1360 and the fit results are stored in memory 1370. If another angle scan is desired 1380, the procedure returns to step 1320; otherwise, the fit stage completes.

Initialize and Self-Test 1310. In the preferred embodiment, the detailed operation of the EPF fit software is controlled by a set of control parameters. Default values of these parameters are contained within the program and set by the fit initialization routine. Optionally, the control software may retrieve the current parameter set and/or set new values. The initialization routine also initiates a complete test of the EPF Fit module from end-to-end using various test procedures, which in turn employ randomized synthetic data generated by a procedure from the calibration module. The test results are verified for correctness. In the preferred embodiment, the initialization process also includes setting the fit initialization flag.

Perform Run. After acquiring a calibration set, a run is generally performed in which a sequence of angle scans is made in order to track the time evolution of the SPR angle responses of the several (typically 100-400 or more) ROIs on the chip as various buffer and sample solutions are flowed over it. The resulting SPR responses will later be analyzed to determine the events and parameters of interest, such as binding affinities, kinetic rate constants, etc.

Acquire Runtime Angle Scan at time t 1320. For each time point during an SPR run, which may last from a minute or two to several hours or more (but is typically 20-200 minutes, depending on the time scales of the chemical reaction rates involved), an angle scan is performed, followed by EPF fits to determine the resonance angles for each of the ROIs. Fitting is typically overlapped in time with data acquisition of the next time point.

The SPR signal is measured for each ROI as a function of angle of incidence over a range sufficient to include all resonances on the chip. This range may be similar to, greater than, or less than the angle range used for the calibration step. In the preferred embodiment, it may be changed during the run as needed in order to ensure inclusion of all the ROI resonances as resonances shift in the course of the run. The angle steps are maintained nominally equal at a predetermined value, typically 50 to 200 mDeg or approximately 5-20% of the width (FWHM) of the resonance. Typically, these angle steps are much larger than the steps needed for the calibration procedure.

As in the calibration stage, SPR signals are averaged over the detector pixels defining each ROI, which comprise typically 200 to 4000 pixels each. ROIs may be of any of the various shapes known in the art, including rectangular, elliptical, or annular. As discussed, signals are usually expressed in A/D counts, but any consistent units may be used. In the preferred embodiment, the full signal intensity data set is contained in a two-dimensional array with indices of ROI index and angle index.

A separate vector contains the angle values, preferably angles measured using an angular encoder. Thus actual measured angles, rather than nominal commanded angles, are preferably employed. Another separate vector, not needed for the calibration data set, contains the mean actual clock times at which the individual angle data points (each consisting of one or more CCD detector frames) were obtained. A single CCD exposure is used at each angle value, but multiple frames may be averaged or co-added for enhanced signal/noise.

In the preferred embodiment, during normal operation these data are acquired by the Instrument Control Software and are passed to the main EPF fit routine immediately following each angle scan. However, the EPF may also be used in a post-run mode for reanalysis of data sets, in which case the measured data will have been stored to disc and retrieved.

Extract single ROI scan 1330. Since the epfFit routine of the preferred embodiment processes only one ROI at a time (unlike epfCal, which handles the whole set of ROIs in a single call), the data for each ROI must be separated out by the Instrument Control Software. For each ROI, the ROI index and/or label, a vector of pixel-averaged signal intensities, a vector of encoder angles, and a vector of frame measurement times is prepared and employed for the fit routine call. Note that the last two vectors remain the same across all ROIs for each scan, but will change from scan to scan.

Process one Run-Time ROI Scan 1340. This core procedure is described in more detail later, in conjunction with the description of FIG. 14.

Update Graphical Display 1360. In the preferred embodiment, the Instrument Control Software generally displays SPR response (angle) vs. time curves for several or all ROIs in real time so that users can observe the chemical binding curves developing, identify problems, and possibly determine whether to terminate the run early or to extend it.

Store Fit Results to disc 1370. Fit results, including quality measures and error codes, are optionally stored to disc for later detailed analysis. In the preferred embodiment, for each ROI run, results consist of a vector containing, at each time data point, a Results structure containing the following: epfFit Results, ROI label, average step spacing in scan (in degrees), scan inversion flag (True if scan was downward in angle and had to be inverted), angular shift $\Delta\theta$ from calibration profile to this scan, $\theta_{SPR}$ based on nominal calibration profile SPR angle, run time at which resonance minimum was observed, number of angle scan points actually used in fit, RMS residual ($\delta y_{RMS}$), amplitude of fit (should be of order unity), Baseline of fit, extrapolation flag (True if result was extrapolated due to incomplete profile), scan pruned flag (indicates that less than full scan length fitted (usual case)), a Quality of Result parameter (typical possible values being "Excellent", "Good", "Poor", and "Bad"), a description of the primary error condition, if any, and the number of non-fatal warning conditions encountered.

Figure 14:
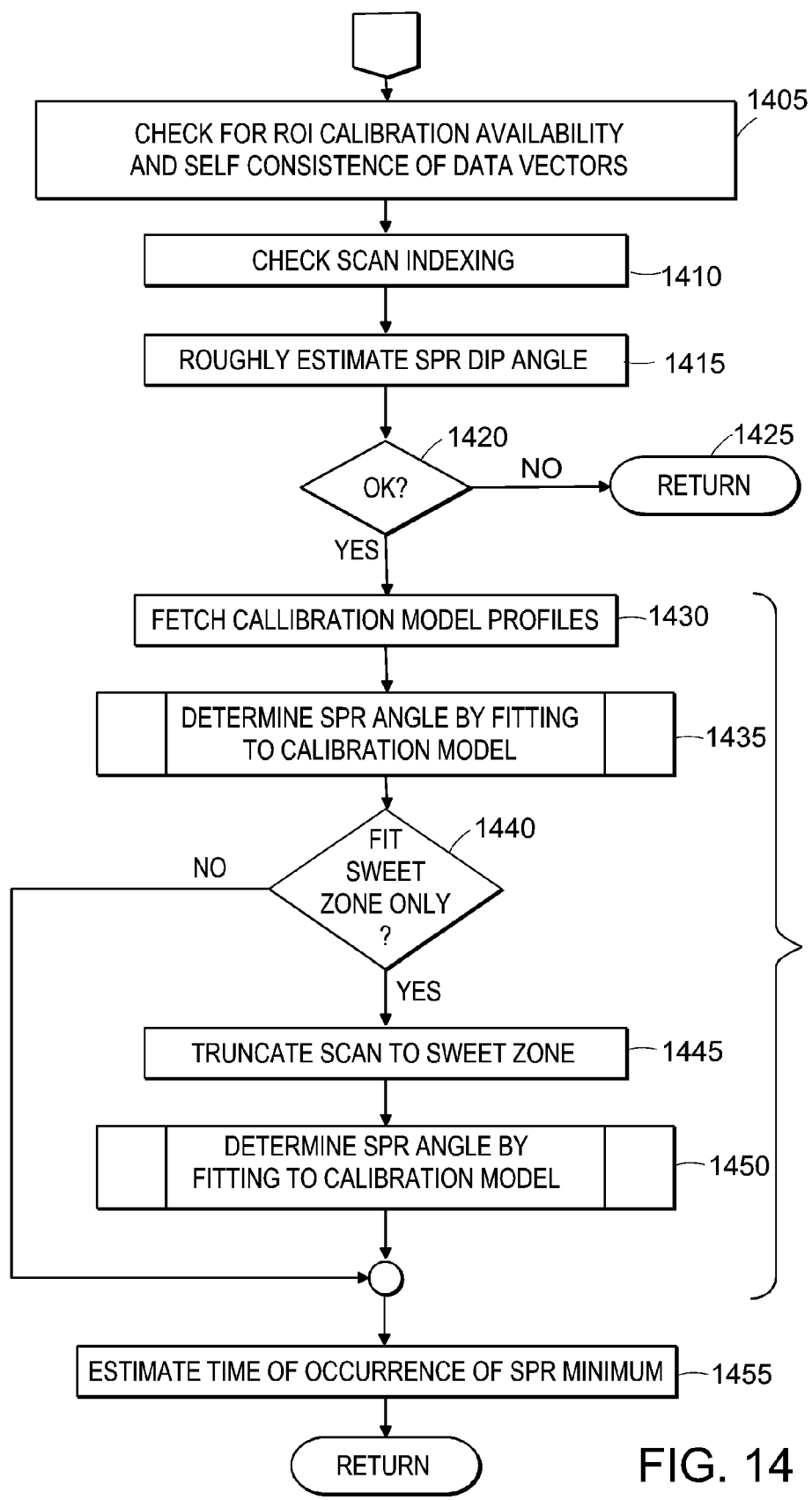
FIG. 14 is an operational flowchart of the processing of one ROI scan.

FIG. 14 is an operational flowchart of the processing of one ROI scan, as shown in step 1340 of FIG. 13. Each of the steps is described in more detail in the text that follows. A description of the implementation of the preferred embodiment is presented at the end of the Detailed Description section.

As shown in FIG. 14, initially the availability of a calibration profile for the ROI and the self-consistency of the extracted data vectors are checked 1405, the scan indexing is checked 1410, and the SPR dip angle is roughly estimated 1415 to make sure it is within the scan range. If any of these tests fail 1420, the processing is stopped and an error is returned 1425. Otherwise, the calibration model profile for the ROI is fetched 1430 and the SPR angle is determined by fitting to the calibration model 1435. If a Sweet Zone fit is requested 1440, the scan is truncated 1445 and the SPR angle is recalculated by fitting the truncated scan to the calibration model 1450. Finally, the time of occurrence of the SPR minimum is estimated 1455.

Check for Calibration Availability 1405. In the preferred embodiment, a consistency check procedure is used to verify that the signal intensity, scan angle, and time of measurement vectors are all consistently indexed. Next, it is verified that a current calibration set exists and corresponds to the Chip ID of the current data, and that a calibration profile for the specified ROI exists and is valid. If there is a problem, appropriate error flags for this ROI are set.

Check Scan Indexing 1410. In the preferred embodiment, if the sense of the scan is reversed (i.e., from large to small angles of incidence), then a working copy of the three data vectors with the correct sense is generated. This may happen on alternate scans when using bi-directional scanning, which speeds up data acquisition. This routine also checks that the angle steps are monotonic and sufficiently consistent in magnitude, that there are a sufficient number of angular data points, that a sufficient angle range is covered by the scan, and that the time of measurement values are monotonic in time.

Roughly Estimate SPR Angle 1415. Initially, a first estimate of the angular location of the resonance is generated. First, the minimum intensity point in the scan is located. Depending on the settings of certain control parameters, the minimum may be required to fall within the scan and at least a certain specified distance from the ends, or, alternatively, extrapolation may be permitted and the resonance position may be allowed to fall outside the scan range. If the minimum is not too close to either end of the scan, according to these settings, then the scan is qualified. If the minimum is at least one data point from each end of the scan, then a quadratic fit is used to estimate an interpolated angular minimum. If not, then the minimum itself is used as the rough estimate. This roughly estimated SPR angle is used as a starting point to facilitate the fitting process below. Other methods known in the art for roughly estimating the SPR angle would also be suitable.

Figure 15:
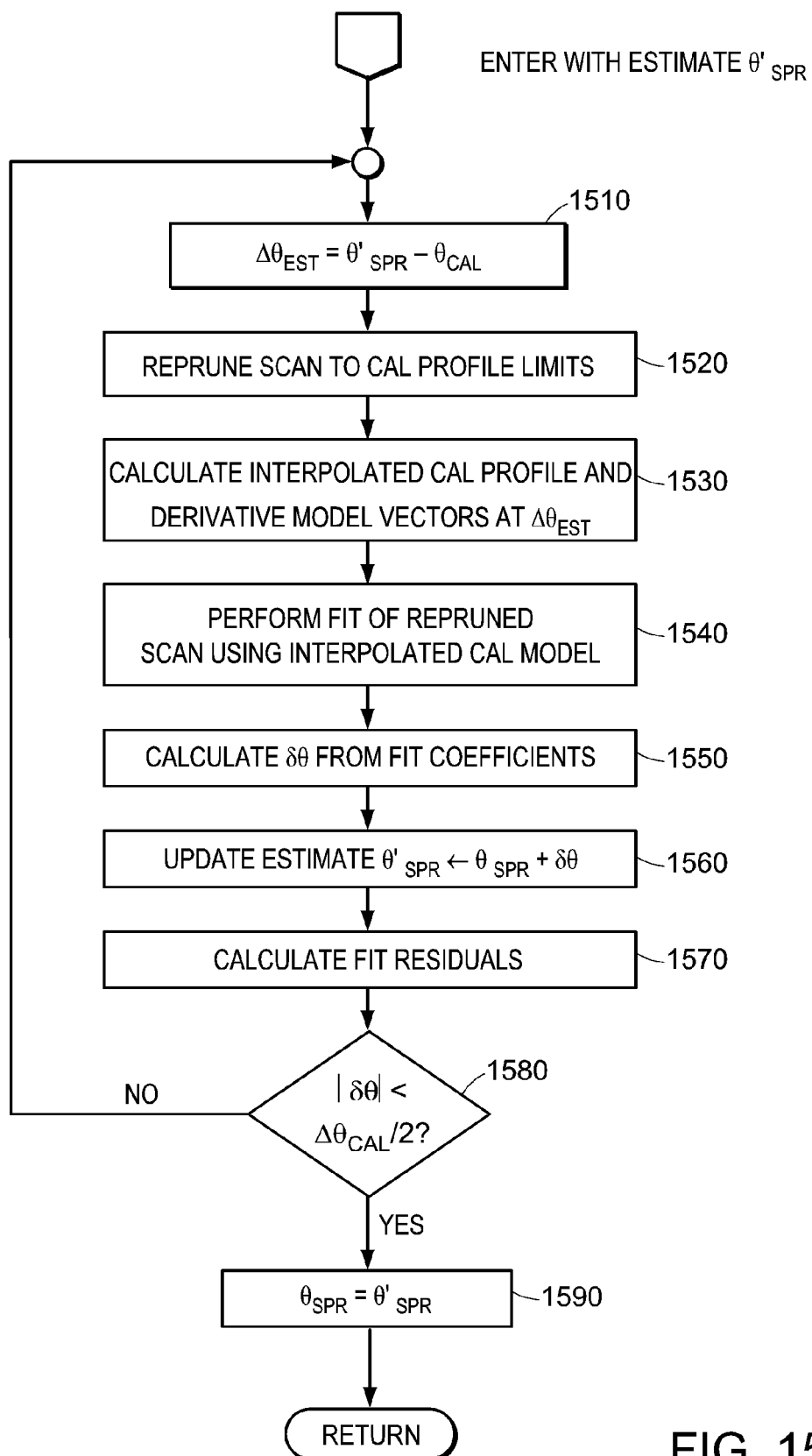
FIG. 15 is an operational flowchart of the determination of the resonance angle utilizing an empirical profile fit.

Accurate Determination of SPR Angle 1435, 1450. This core fitting procedure is described in more detail later, in conjunction with the description of FIG. 15. First, the appropriate calibration model profile and derivative vectors are fetched from memory. Next, the fit calculation "Determine SPR Angle by fitting to Calibration Model", described in detail conjunction with FIG. 15, is performed once, using the full scan range. Then, if a Sweet Zone fit has been requested, the scan range is pruned to the specified Sweet Zone range on either side of the first calculated SPR angle, and the core fitting procedure is repeated to find the final result. This iteration is performed because the initial full range fit is more robust than the limited range Sweet Zone fit, and is thus better able to find the approximate resonance angle without potentially being "fooled" by anomalies in the data or by a highly inaccurate initial estimate. On the other hand, the Sweet Zone fit may be specified to further refine and optimize the fit, since it is less influenced by possible shape artifacts in the far wings of the scan data.

Truncation to the Sweet Zone 1445. In the preferred embodiment, truncation to the Sweet Zone is carried out in two steps. First, a procedure determines whether the scan is already too short on one end or the other to encompass the putative Sweet Zone. If so, the angular limits of the Sweet Zone are shifted away from the short end if possible, in order to maintain the full angular width of the Sweet Zone. In the second step, another procedure carries out the actual truncation.

Estimate Time of Minimum 1455. Knowing the fractional data point at which the SPR resonance was found, in the preferred embodiment the time of measurement is interpolated in order to determine the time in the run at which this ROI's SPR minimum occurred. It is not sufficient to simply use the start time or the midpoint of the angle scan, since some ROIs may have minima near the beginning of the scan and others near the end. Accurate times are important in later analysis of kinetic binding curves.

Core Fitting Procedure. FIG. 15 is an operational flowchart of the determination of the SPR angle utilizing an empirical profile fit, as discussed in steps 1435 and 1450 of FIG. 14.

Each of the steps is described in more detail in the text that follows. A description of the implementation of the preferred embodiment is presented at the end of the Detailed Description section.

As shown in FIG. 15, the estimated offset of the run-time SPR resonance angle from the calibration scan for the same ROI is computed 1510, and the scan is repruned to the calibration profile limits 1520. Next, the calibration profile is interpolated and the derivative model vectors are calculated at the estimated offset 1530. A fit is performed on the repruned scan using the interpolated calibration profile 1540 and the residual angular shift from the estimated shift is calculated from the fit coefficients 1550. An improved estimate of the SPR resonance angle is calculated 1560, as are the fit residuals 1570. While in the preferred embodiment, this fit loop is iterated until the magnitude of the angle shift is less than half the subsample angle step spacing in the calibration profile 1580, any suitable convergence criterion may be advantageously employed. Iteration will take place until the value of the resonance shift converges to the predetermined convergence criterion.

In the preferred embodiment, the basic SPR angle determination is carried out by a procedure, which is called twice. On entry, this procedure is supplied with the calibration model profile and derivative, as well as an initial estimate $\theta'_{SPR}$ of the SPR resonance angle. On exit, it returns a Results structure.

$\Delta\theta_{EST}=\theta'_{SPR}-\theta_{CAL}$ 1510. The estimated offset $\Delta\theta_{EST}$ of the SPR resonance from its location in the calibration scan is computed in order to allow appropriate shifting of the model components.

Reprune Scan to Cal Profile Limits 1520. In general, the current angle scan may extend beyond the range covered by the calibration model on one or both ends. Accordingly, the scan is temporarily truncated to a range that does lie within the Calibration range, as determined using the current estimated angle offset, $\Delta\theta_{EST}$. Note that points temporarily pruned off may be restored on later iterations.

Calculate Interpolated Cal Profile 1530. Calculate Interpolated Cal Profile 1530 is one of the more delicate parts of the fit algorithm. Based upon the current estimated angle offset, $\Delta\theta_{EST}$, the subsampled calibration model profile and its derivative are shifted an integer number of subsampled angle steps (which are typically 10 mDeg) in order to bring them into the closest possible alignment with the estimated position of the scan being fitted. Then the model profile and derivative are interpolated to the actual irregularly spaced measured angle values of the repruned scan being fitted using Lagrange interpolation. For end points, $2^{nd}$ order Lagrange interpolation is used, while for interior points in the pruned scan, $4^{th}$ order Lagrange interpolation is employed. At this point, resampled calibration profile and derivative models have been created at the estimated shift of the scan being fitted. While Lagrange interpolation is used in the preferred embodiment, many other methods known in the art would be suitable.

Perform Least Squares Fit of Repruned Scan 1540. In the preferred embodiment, the pruned scan is subjected to a classical linear least squares fit using three components:
1. The resampled calibration profile
2. The resampled calibration derivative
3. A constant baseline offset The third component is not strictly necessary, but is recommended to accommodate baseline system drift and other instrumental effects. Additional components can be included to accommodate intensity drift and other instrumental artifacts, although some may potentially degrade rather than improve estimates of the angle shift. The fit model is:

$$y_{FIT}=C_0 y_{PROFILE}+C_1 y_{DERIV}+C_2$$

Calculate $\delta\theta$ from Fit Coefficients 1550. The residual angular shift $\delta\theta$ from the estimated angle used to resample the calibration profile is proportional to the fit coefficient for the derivative component. More specifically, $$\delta\theta=-C_1/C_0$$

where $C_0$ and $C_1$ are the first and second model component fit coefficients respectively.

Update Angle Estimate 1560. The improved estimate of the SPR resonance angle is calculated as:

$$\theta'_{SPR}{}^{NEW} \leftarrow \theta'_{SPR}+\delta\theta$$

Calculate Fit Residual 1570. The residuals are computed as $\delta y_i = y_{OBSERVED\ i} - y_{FIT\ i}$, and the rms residual value is computed as $$\delta y_{RMS}=[\Sigma \delta y_i^2]/DoF$$

where the number of degrees of freedom $DoF=N_{POINTS}-N_{COMPONENTS}$, with $N_{COMPONENTS}=3$.

$|\delta\theta|<\Delta\theta_{CAL}/2$? 1580. In the preferred embodiment, the iteration of the fit loop is terminated when the magnitude of the angle shift $\delta\theta$ is less than half the subsample angle step spacing in the calibration profile, indicating that the integer point shift was as close as possible to the true shift. In most cases, only one pass through the loop is needed, but if the initial guess was poor, one or more further iterations may be required.

The loop termination criteria also include the possibility of oscillation, in case the fitted angle value is very nearly half way between two subsampled calibration profile points. It is then possible that the value of $|\delta\theta|$ might stay slightly above $0.5\ \Delta\theta_{CAL}$ as the integer offset oscillates between two adjacent values on successive iterations. In the preferred embodiment, if the algorithm becomes trapped in such a loop, it exits after several iterations, and the lowest observed value of $|\delta\theta|$ is used. Note that although this is the preferred termination criterion, other less restrictive termination criteria, such as $|\delta\theta|<\Delta\theta_{CAL}$, can be used with reasonable success.

Generate Results 1590. $\theta_{SPR}=\theta'_{SPR}$. The final value of the fitted angle estimate, on the final pass through the angle fit procedure, is taken as the result. The corresponding rms residual is also reported. The Results structure for each ROI is created. It will later optionally be stored to disc.

Figure 16:
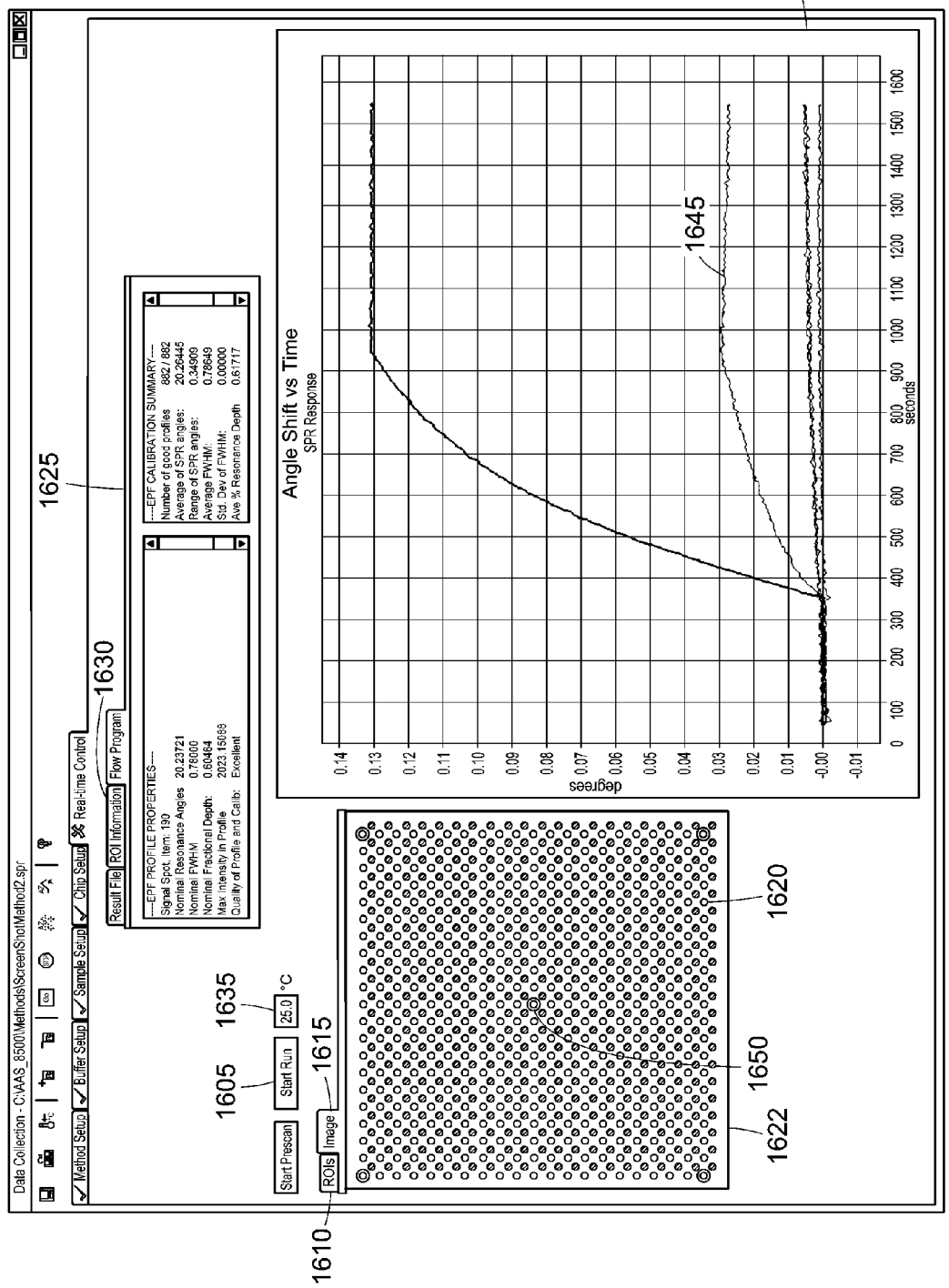
FIG. 16 is a screenshot depicting an example output from the fit stage.

FIG. 16 is a screenshot depicting an example output from the fit stage. It must be appreciated that the screen embodiment depicted in FIG. 16 is provided by way of example only and that additional parameters or graphics may be added, parameters or graphics may be deleted, or alternate screen configurations may be employed without departing from the invention. This screen is similar to the screens depicted in FIGS. 9 to 11, but is shown during an actual run, which was initiated using the Start Run button 1605 at the left.

As shown in FIG. 16, the ROIs Tab 1610, rather than Image tab 1615, is selected. The various ROIs 1620 shown on the ROIs map 1622 have been spotted with various ligands. Visible at the top of the screen are the EPF profile properties for ROI 190 and the EPF prescan summary 1625, selected by clicking on the "ROI Information" tab 1630. The run temperature is shown in box 1635. In this case, the large graph at the lower right 1640 displays not Intensity vs. Angle, but rather Angle Shift vs. Time as the experiment progresses. Again, a subset of the ROI curves 1645 is displayed, corresponding to the highlighted ROIs 1650 on the ROIs map 1622. Individual data points on this plot each correspond to a complete angle scan, from which EPF calculates a resonance angle position. In this case, new points are plotted approximately every 6 seconds, so that the points are too closely spaced to be resolved on this scale. Because of this, symbols are not plotted; only the connecting line segments are displayed.

During the run displayed, the various ROI plots are autozeroed at the beginning of the run, with only the deviations from the initial angles being displayed. At 300 sec, a sample is introduced and binding to the surface commences, to different degrees on the various ROIs. At t=900 sec, the sample flow is turned off, the buffer flow is reinstated, and the bound sample begins to slowly dissociate from the surface.

These sorts of kinetic curves (association phase and dissociation phase) are what are further analyzed, in postprocessing, to generate the desired measurements of kinetic binding constants. In the preferred embodiment, this analysis is not done on the instrument, using the instrument control software, but instead the fit data are exported to other specialized tools. Displays of the finished data can be readily generated using these other tools.

Alternate Configurations. It is feasible to use tabulated theoretical model functions in the EPF formalism, as if they had been measured. In other words, the calibration scans may be performed as in EPF, theoretical response curves may be fitted to these measured curves, and then the fitted curves may be used as the EPF model functions. In effect, this provides an alternative means of performing the smoothing operation in deriving EPF models. If the experimental profiles are clean enough to be accurately modeled by the theory, this works well—but probably not significantly better than the EPF approach. The computational overhead might possibly be acceptable, since the nonlinear fits need be done only once per run, per ROI. There is a large increase in software complexity, however, with little or no benefit. In addition, Explicit Functions, if suitable ones can be identified, may be used as stand-ins for empirical profiles, and work about as well as empirical profiles in the EPF approach.

Although the above description of the preferred embodiment refers to an angle scanned optical resonance system, as previously discussed, the same procedures may be applied to a wavelength-scanned system. In such case, references to "angles" and "angle steps" are replaced by "wavelength" and "wavelength steps". In addition, references to "encoder angles" are replaced by "calibrated wavelength values". It will also be appreciated that the numerical values and units of Wavelength Step sizes are different, such as "0.5 nm" instead of "0.05 degree". The resonance shift is therefore a wavelength shift instead of an angle shift. Similarly, the EPF system of the present invention can be applied to data obtained from predispersion or correlated scanning, with appropriate changes being made to the referenced parameters. Further, while use of calibration profile derivatives to determine the resonance shift is currently the preferred embodiment of the present invention, other methods known in the art would also be suitable and are contemplated as being within the scope of the present invention.

Error Reporting. The preferred embodiment of the invention also includes an error-reporting function. Error reporting may be handled through any of the many methods known in the art. Errors may be reported during either the calibration or the fitting stage, or both. In one embodiment, an error severity level is specified above which an error will be logged. Optionally, a number of errors detected during the calibration stage that is above a specified threshold may result in rejection of the calibration scan or of the chip itself.

As an example, FIG. 17 is a screenshot depicting an example embodiment of a local error log, showing reports of bad fits to particular ROIs. It must be appreciated that the screen embodiment depicted in FIG. 17 is provided by way of example only and that additional parameters may be added, parameters may be deleted, or alternate screen configurations may be employed without departing from the invention. As seen in FIG. 17, in this embodiment the error log reports the date/time 1710 of error, the application 1720 generating the error, the error severity 1730, the user 1740, the module 1750 generating the error, an indicator 1760 showing whether the error was caused by bad data received or by some other type of event, and a description 1770 of the error.

Figure 18:
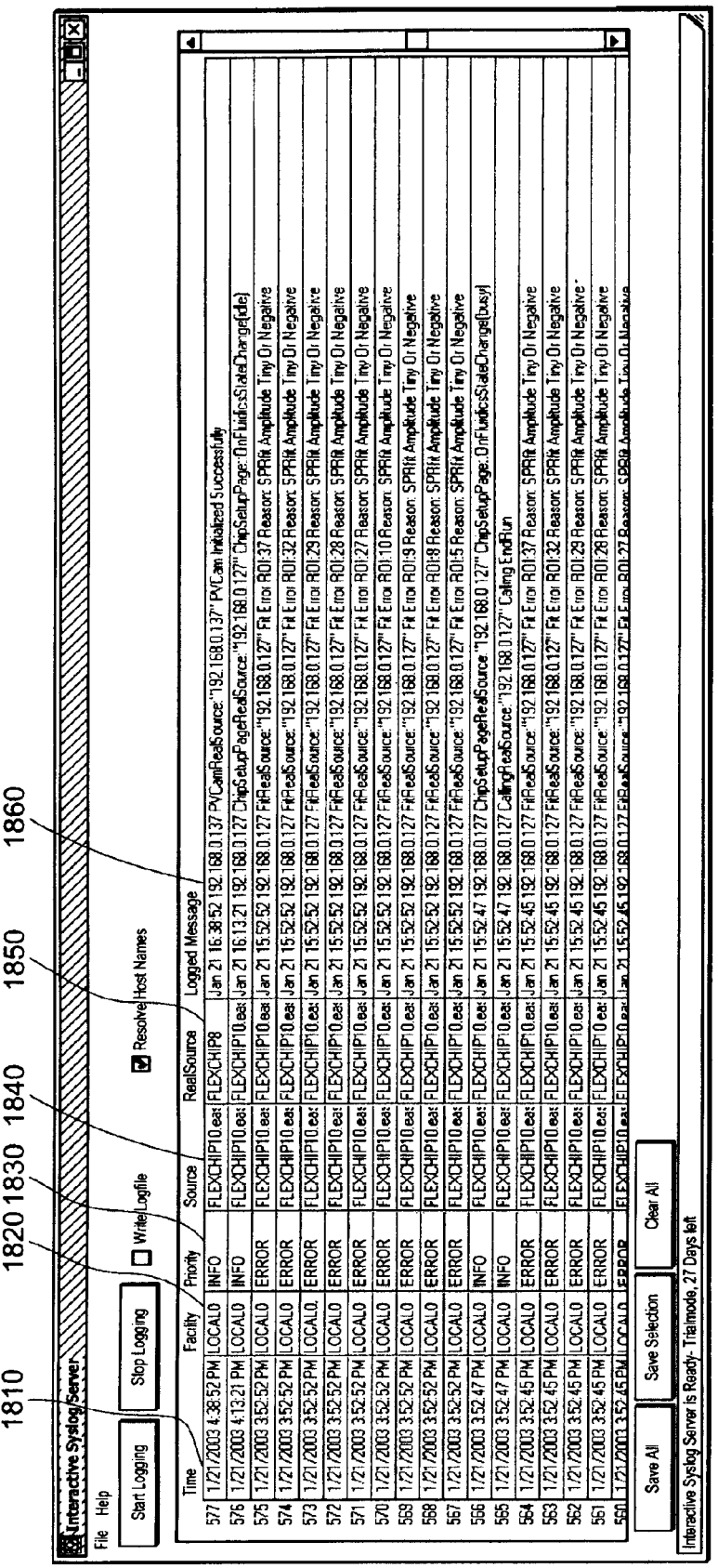
FIG. 18 is a screenshot depicting an example embodiment of an error log on a remote networked supervisory computer, showing reports of bad fits to particular ROIs.

FIG. 18 is a screenshot depicting an example embodiment of an error log on a remote networked supervisory computer, showing reports of bad fits to particular ROIs. It must be appreciated that the screen embodiment depicted in FIG. 18 is provided by way of example only and that additional parameters may be added, parameters may be deleted, or alternate screen configurations may be employed without departing from the invention. As seen in FIG. 18, the error log reports the time 1810 of the error, the facility 1820 generating the error, the error priority 1830, the apparent error source 1840, the real error source 1850, and the logged error message 1860.

Implementation of the Preferred Embodiment. While the present invention may be implemented by any suitable method, mechanism, or combination of methods and/or mechanisms known in the art, it is preferably implemented in software. In the preferred embodiment, the software source code is implemented using Visual Basic or C++, but any suitable programming language or tool of software implementation known in the art is also within the scope of the invention. Similarly, the software may be run utilizing any suitable operating system, compiler, interpreter, application program, or other such device known in the art. In the preferred embodiment of the invention, the actual product shipped consists of object code and associated Dynamic Link Libraries (DLLs).

Exposed Methods for Calibration. In the preferred embodiment, many procedures are Boolean Functions returning True on failure, except as indicated. An Error Code of type Long is also generally returned. Many procedures are optional; the two that are essential are the calibration initialization procedure and the main calibration module. The calibration initialization procedure must be called before any other action. It initializes the calibration module, sets default values for the calibration parameters, and performs an end-to-end self test of the calibration module.

The main calibration procedure performs the calibration, storing the results in its own memory. It does not fail unless a fatal error is encountered. Thus, one or more ROIs may fail without causing the whole procedure to collapse. The number of ROIs for which a problem was encountered is returned. The problem may range from outright failure to a poor rating based on various quality measures. The calling program should check whether the number of ROIs for which a problem was encountered is >0, and, if so, investigate.

Exposed Methods for Fitting. In the preferred embodiment, only one ROI is fitted per call. This allows flexibility, in that other work can be done in between ROI fits, such as plotting results incrementally. In addition, this allows more detailed error and problem reporting on a per ROI rather than global basis. Fitting is more complex and tricky than calibration, but there is only one basic method involved. Again, most procedures are Boolean Functions returning True on failure. Only two procedures are mandatory, the EPF initialization procedure and the main fit module. The fit initialization procedure must be called before any other action. It initializes the fit module and sets default values for the fit parameters. The main fit routine is a Boolean Function, returning True if any trouble was encountered. This does not necessarily mean that the result is useless; results must instead be inspected for details.

In the preferred embodiment, time is measured in seconds from the initiation of a run. In some cases, the times are actually stored as minutes for easy human interpretation. For example, the affinity plots now have the lower time scale in minutes. The measurement time values received by the epfFit routine need not be highly accurate. They are used to provide more accurate estimates of the time axis for dynamic situations such as kinetic analysis. Probably values accurate to 0.1 sec are adequate, although somewhat better values may be useful. These times are normally reported in seconds, according to some system clock that runs continuously during a kinetic run and will be used to plot and analyze kinetic data. Time of day in seconds would also be acceptable, except that it will "reset" at midnight and could therefore corrupt a run taken at that time.

The apparatus and method of the present invention, therefore, provide a new mechanism for quantitation of surface-binding optical resonance curves that has relatively low computational complexity, requires a minimal number of scan data points, is less sensitive to shot noise, accommodates the use of long scan times, provides increased scan speeds, provides results for a sample quickly, accommodates scans over a greater number of ROIs, and provides useful results even when only partial curves are available. Each of the various embodiments described above may be combined with other described embodiments in order to provide multiple features. Furthermore, while the foregoing describes a number of separate embodiments of the apparatus and method of the present invention, what has been described herein is merely illustrative of the application of the principles of the present invention. Other arrangements, methods, and substitutions by one of ordinary skill in the art are therefore also considered to be within the scope of the present invention, which is not to be limited except by the claims that follow.

What is claimed is:

1. An apparatus for quantitation of surface-binding optical resonance profiles comprising, in combination:
    calibration module, said calibration module comprising:
        calibration scan result fetcher for generating a calibration profile of a region of interest on a surface plasmon resonance chip being tested; and
        calibration profile creation module for smoothing and subsampling the calibration profile to generate model calibration profiles for a plurality of regions of interest on the surface Plasmon resonance chip; and
    fitting module, said fitting module comprising:
        experimental scan result fetcher to obtain an experimental region of interest scan profile;
        calibration profile fetcher to measure an angle shift between experimental region of interest scan profile and the model calibration profile; and
        resonance shift determination module outputting resonance parameters related to the surface plasmon chip being tested.

2. The apparatus of claim 1, wherein said calibration profile creation module further includes a curve smoother.

3. The apparatus of claim 1, wherein said calibration profile creation module further includes a subsampler.

4. The apparatus of claim 1, wherein said calibration profile creation module further includes a curve smoother and a subsampler.

5. The apparatus of claim 1, further including a resonance parameter calculator.

6. The apparatus of claim 5, wherein the calculated resonance parameters are selected from the group consisting of estimated absolute resonance point, time of resonance minimum, diagnostic information, and quality information.

7. The apparatus of claim 1, further including an instrument control and data acquisition module.

8. The apparatus of claim 7, further including a test and support module.

9. A method for qualifying a surface plasmon resonance chip comprising:
    obtaining a single golden calibration profile for the type of surface plasmon chip to be qualified, the golden calibration profile being based on a set of surface plasmon resonance profiles acquired from a plurality of surface plasmon chips;
    obtaining at least one calibration result from a calibration scan of at least one Region of Interest of the surface plasmon chip to be tested;
    comparing said at least one calibration result to said golden calibration profile to obtain at least one comparison result; and
    determining whether said surface plasmon chip is suitable for use by applying selection criteria to said at least one comparison result.

10. The method of claim 9, further including displaying chip qualification results to the user.

11. The method of claim 10, wherein determining whether the chip is suitable includes incrementing a bad region of interest (ROI) count.

12. The method of claim 11, wherein determining whether the chip is suitable includes storing a bad region of interest (ROI) number for display.

13. The method of claim 9, wherein comparing the calibration includes initializing a fit module with a chip qualification parameter set.

14. The method of claim 9, wherein obtaining a golden calibration profile further comprises averaging together the plurality of surface plasmon resonance profiles to generate the golden calibration profile.

15. The method of claim 14, wherein obtaining a plurality of surface plasmon resonance profiles further comprises:
    generating a surface plasmon resonance profile for a plurality of surface plasmon resonance chips;
    determining a quantity of data points and a full width at half maximum (FWHM) value for each of the surface plasmon resonance profiles; and
    assigning a surface plasmon resonance profile to the set of the surface plasmon resonance profiles when the quantity of data points and the full width at half maximum (FWHM) value each exceed a predetermined value.

* * * * *